US009314498B2

(12) United States Patent
Nikawa

(10) Patent No.: US 9,314,498 B2
(45) Date of Patent: Apr. 19, 2016

(54) **BACTERIOCIN DERIVED FROM *LACTOBACILLUS RHAMNOSUS***

(71) Applicant: Hiroshima University, Hiroshima (JP)

(72) Inventor: Hiroki Nikawa, Hiroshima (JP)

(73) Assignee: Hiroshima University, Hiroshima (JP)

( * ) Notice: Subject to any disclaimer, the term of this patent is extended or adjusted under 35 U.S.C. 154(b) by 0 days.

(21) Appl. No.: 14/707,956

(22) Filed: May 8, 2015

(65) Prior Publication Data

US 2015/0238565 A1    Aug. 27, 2015

Related U.S. Application Data

(63) Continuation of application No. 13/984,783, filed as application No. PCT/JP2012/053020 on Feb. 9, 2012, now abandoned.

(30) Foreign Application Priority Data

Feb. 10, 2011    (JP) .................................. 2011-027882
Aug. 26, 2011    (JP) .................................. 2011-184655

(51) Int. Cl.
*A61K 38/16* (2006.01)
*C07K 14/335* (2006.01)
*C12P 21/02* (2006.01)
*C12R 1/225* (2006.01)

(52) U.S. Cl.
CPC .............. *A61K 38/164* (2013.01); *C07K 14/335* (2013.01); *C12P 21/02* (2013.01); *C12R 1/225* (2013.01)

(58) Field of Classification Search
None
See application file for complete search history.

(56) References Cited

U.S. PATENT DOCUMENTS

2014/0128314 A1    5/2014    Nikawa

FOREIGN PATENT DOCUMENTS

| EP | 2455095 A1 | 5/2012 |
| WO | 2005955445 A1 | 10/2005 |
| WO | 2011007584 A1 | 1/2011 |
| WO | 2012108518 A1 | 8/2012 |

OTHER PUBLICATIONS

Dictionary.com "prophylaxis" definition (accessed Sep. 30, 2015).*
Gorr et al. (Journal of Clinical Periodontology, vol. 38 (s11), epub Feb. 16, 2011).*

Extended European Search Report, Mailed on Oct. 28, 2014, for EP-12745195.3.
Helmerhorst, Eva J., et al., "Synthetic Histatin Analogues with Broad-Spectrum Antimicrobial Activity", Biochemical Journal, Portland Press Ltd., GB, vol. 326, No. 1, pp. 39-45, Aug. 15, 1997.
Database UniProt [Online], "SubName: Fuii=Uncharacterized Protein", Retrieved from EBI Accession No. UNIPROT: C2JW85, Jun. 16, 2009.
Singh et al. (Indian Journal of Dental Advancement, 3(3), 2011, epub Oct. 2011 ).
Hiyama et al., 12. Preventive effects of lactic acid bacterial strain derived from oral cavity against Mutans streptococci and Candida. Fourth-Year Students, Division of Oral Health Engineering, Faculty of Dentistry, Hiroshima University, vol. 41, No. 1, 93-94 (2009). (English translation provided).
International Search Report and Written Opinion for International Application No. PCT/JP2012/053020 filed on Feb. 9, 2012.
Shiokawa et al., 5. Search for antimicrobial substance producing bacteria from Lactobacillus bacteria derived from human oral cavity. Undergraduate Fourth-year, Infection and Immunity Course, vol. 32, No. 3/4, 3, 5 (2006). (English translation provided).
UniProt sequence C2K1D4 (integrated into UniProtKB Jun. 19, 2009).
Oyston et al. (Journal of Medical Microbiology (2009), 58, 977-987).
Dover et al. (Safety Study of an Antimicrobial Peptide Lactocin 160, produced by the Vaginal Lactobacillus rhamnosus, Infectious Diseases in Obstetrics & Gynecology 2007).
Dimitrijevic et al. "The identification of a low molecular mass bacteriocin. rhamnosin A, produced by Lactobacillus rhamnosus strain 68." Journal of Applied Microbiology 107 (2009) 2108-2115.
Dunsche et al. "The novel human beta-defensin-3 is widely expressed in oral tissues." European Journal of Oral Sciences, 110, pp. 121-124, 2002.
Kankainen et al. "Comparative genomic analysis of Lactobacillus rhamnosus GG reveals pili containing a human-mucus binding protein." PNAS, Oct. 6, 2009, vol. 106, No. 40, 17193-17198.
Morita et al. "Complete Genome Sequence of the Probiotic Lactobacillus rhamnosus ATCC 531 03." Journal of Bacteriology, Dec. 2009, p. 7630-7631, vol. 191, No. 24.
Todorov et al. "Screening for bacteriocin-producing lactic acid bacteria from boza, a traditional cereal beverage from Bulgaria, Comparison of the bacteriocins." Process Biochemistry 41 (2006) 11-19.

* cited by examiner

*Primary Examiner* — James H Alstrum Acevedo
*Assistant Examiner* — Tara Martinez
(74) *Attorney, Agent, or Firm* — K&L Gates, LLP; Louis Cullman; Michelle Glasky Bergman

(57) ABSTRACT

Provided is a bacteriocin that is capable of being easily mass-produced, has high antimicrobial activity even at low concentration, has a wide antimicrobial spectrum, and is less likely to produce resistant microorganisms. The bacteriocin has the amino acid sequence shown in SEQ ID NO: 1 or SEQ ID NO: 2 in SEQUENCE LISTING, or has the same amino acid sequence as shown in SEQ ID NO: 1 or SEQ ID NO: 2 in SEQUENCE LISTING except that one or several amino acids are deleted, substituted, inserted and/or added, wherein the amino acid sequence provides antimicrobial activity and the isoelectric point is not less than 12.

11 Claims, 15 Drawing Sheets

KO1 ALONE    KO1 +
             KILLED CELLS OF CaGDH18

Kog2

KO1 ALONE

KO1 +
KILLED CELLS OF CaGDH18

BACTERIOCIN DERIVED FROM LACTOBACILLUS RHAMNOSUS

CROSS REFERENCE TO RELATED APPLICATIONS

The present application is a continuation of U.S. Ser. No. 13/984,783 filed Aug. 9, 2013, which is an application under section 371 of International Patent Application No. PCT/JP2012/05320 filed Feb. 9, 2012, which claims priority to Japanese patent applications 2011-027882 filed Feb. 10, 2011 and 2011-184655 filed Aug. 26, 2011, the entire disclosures of all of which are incorporated by reference herein in their entirety.

TECHNICAL FIELD

The present invention relates to a bacteriocin that produces antimicrobial activity against causal microorganisms of oral diseases, a composition for prophylaxis, amelioration and/or therapy of oral diseases comprising the bacteriocin as an effective component, a gene encoding the bacteriocin, a recombinant expression vector obtained by incorporation of the gene, a host cell comprising the recombinant expression vector, a transformant produced by transformation with the recombinant expression vector, a method for producing the bacteriocin, and a novel lactic acid bacterial strain that produces the bacteriocin, the *Lactobacillus rhamnosus* KO1 strain.

BACKGROUND ART

Currently, association of oral diseases such as dental caries and periodontal diseases with the general health is drawing attention. Thus, as therapeutic methods for oral diseases such as dental caries and periodontal diseases, various peptides that exert antimicrobial activity against these causal microorganisms have been developed. For example, Non Patent Literature 1 describes ramnosin A, which is a low-molecular-weight bacteriocin produced by the *Lactobacillus rhamnosus* 68 strain.

Further, separation and identification of novel lactic acid bacteria that exert antimicrobial activity against causal microorganisms of oral diseases such as cariogenic bacteria and periodontal disease bacteria have been intensively carried out in recent years. For example, the present inventor previously proposed novel lactic acid bacterial strains, the *Lactobacillus rhamnosus* KO3 strain (L8020 bacterium), the *Lactobacillus casei* YU3 stain and the *Lactobacillus paracasei* YU4 strain, which are capable of producing a fermentation product having a wide antimicrobial spectrum against causal microorganisms of oral diseases and having excellent flavor and palatability (see Patent Literature 1). In addition, as therapeutic methods for oral diseases other than techniques of antimicrobial peptides and isolated lactic acid bacterial strains, therapeutic methods using antibiotics have been proposed.

CITATION LIST

Patent Literature

Patent Literature 1: WO 2011/007584

Non Patent Literature

Non Patent Literature 1: R. Dimitijevic, M. Stojanovic, I. Petersen, R. M. Jankov, L. Dimitrijevic, M. Gavrovic-Jankulovic, 2009, Journal of Applied Microbiology (107), 2108-2115

SUMMARY OF INVENTION

Technical Problem

However, since most of the above-mentioned various antimicrobial peptides are peptides derived from a mammal including human and artificially synthesized peptides, mass production of these peptides is not easy. Moreover, since the antimicrobial activity of such an antimicrobial peptide is low at low concentration, the peptide needs to be used at high concentration, that is, in a large amount.

Further, therapeutic methods using antibiotics sometimes fail to produce the therapeutic effect because of appearance of multiple-drug-resistant bacteria due to abuse of the antibiotics. Therefore, a novel bacteriocin that is capable of being easily mass-produced, has high antimicrobial activity even at low concentration, and is less likely to produce resistant microorganisms, is demanded.

Solution to Problem

The present invention was made under the above circumstances, and aims to provide a bacteriocin that is capable of being easily mass-produced, has high antimicrobial activity even at low concentration, and is less likely to produce resistant microorganisms. Further, the present invention also aims to provide a composition for prophylaxis, amelioration and/or therapy of oral diseases comprising the bacteriocin (including pharmaceutically acceptable derivatives and the like thereof) as an effective component, a gene encoding the bacteriocin, a recombinant expression vector obtained by incorporation of the gene, a host cell comprising the recombinant expression vector, a transformant produced by transformation with the recombinant expression vector, a method for producing the bacteriocin, and a novel lactic acid bacterial strain that produces the bacteriocin, the *Lactobacillus rhamnosus* KO1 strain.

As a result of intensive study, the present inventor discovered that a peptide having the amino acid sequence shown in SEQ ID NO: 1 (hypothetical protein HMPREF0539_2969, accession No. ZP_04442437.1, hereinafter referred to as Kog1) and a peptide having the amino acid sequence shown in SEQ ID NO: 2 (hypothetical protein HMPREF0539_1169, accession No. ZP_04440638.1, hereinafter referred to as Kog2) produced in the *Lactobacillus rhamnosus* KO3 strain (L8020 bacterium) (an application for deposition of the strain was submitted to Patent Microorganisms Depositary, National Institute of Technology and Evaluation (2-5-8 Kazusakamatari, Kisarazu-shi, Chiba 292-0818 Japan) as of Jun. 10, 2009, which was followed by request for conversion to deposition under the Budapest Treaty and then acceptance under accession No. NITE BP-771) proposed in Patent Literature 1 function as bacteriocins having wide antimicrobial spectra and high antimicrobial activity at low concentration, which are less likely to produce resistant microorganisms and have isoelectric points of not less than 12.

Further, as a result of intensive study, the present inventor also succeeded in separation/identification of the *Lactobacillus rhamnosus* KO1 strain (an application for deposition of the strain was submitted to Patent Microorganisms Depositary, National Institute of Technology and Evaluation as of Jan. 24, 2011, and accepted under accession No. NITE P-1065), which is a novel lactic acid bacterial strain that similarly produces Kog1 and Kog2. That is, the present inventor discovered that use of the *Lactobacillus rhamnosus* KO3 strain or the *Lactobacillus rhamnosus* KO1 strain easily allows mass production of the bacteriocins Kog1 and Kog2, which have wide antimicrobial spectra and high antimicrobial activity at low concentration and are less likely to produce resistant microorganisms.

Further, as a result of intensive study, the present inventor elucidated the reason why the bacteriocins Kog1 and Kog2 have wide antimicrobial spectra and high antimicrobial activity at low concentration and are less likely to produce resistant microorganisms. As described in detail in Example 7 below, the reason was that the bacteriocins Kog1 and Kog2 have an action to inactivate endotoxin (LPS, Lipopolysaccharide) of Gram-negative bacteria such as periodontal disease bacteria.

The bacteriocin of the first mode of the present invention has: an amino acid sequence shown in SEQ ID NO: 1 or SEQ ID NO: 2 in SEQUENCE LISTING; or the same amino acid sequence as shown in SEQ ID NO: 1 or SEQ ID NO: 2 in SEQUENCE LISTING except that one or several amino acids are deleted, substituted, inserted and/or added, which amino acid sequence provides antimicrobial activity; which bacteriocin has an isoelectric point of not less than 12.

The bacteriocin preferably has antimicrobial activity against all of cariogenic bacteria, periodontal disease bacteria and *Candida*.

The composition for prophylaxis, amelioration and/or therapy of oral diseases of the second mode of the present invention comprises the bacteriocin of the first mode, or a pharmaceutically acceptable derivative or a pharmaceutically acceptable salt of the bacteriocin as an effective component.

The composition for prophylaxis, amelioration and/or therapy of oral diseases is preferably a growth inhibitor of cariogenic bacteria, periodontal disease bacteria and/or *Candida*.

The gene of the third mode of the present invention encodes the bacteriocin of the first mode.

The recombinant expression vector of the fourth mode of the present invention is obtained by incorporation of the gene of the third mode.

The host cell of the fifth mode of the present invention comprises the recombinant expression vector of the fourth mode.

The transformant of the sixth mode of the present invention is produced by transformation with the recombinant expression vector of the fourth mode.

The transformant is preferably a bacterium.

The method for producing a bacteriocin of the seventh mode of the present invention comprises:

a culture step of culturing *Lactobacillus rhamnosus*; and an extraction step of extracting the bacteriocin of the first mode from a bacterial cell culture obtained by the culture step.

The *Lactobacillus rhamnosus* is preferably a *Lactobacillus rhamnosus* KO1 strain (an application for deposition of the strain was submitted to Patent Microorganisms Depositary. National Institute of Technology and Evaluation (Incorporated Administrative Agency) as of Jan. 24, 2011, and accepted under accession No. NITE P-1065) and/or a *Lactobacillus rhamnosus* KO3 strain (an application for deposition of the strain was submitted to Patent Microorganisms Depositary, National Institute of Technology and Evaluation (Incorporated Administrative Agency) as of Jun. 10, 2009, and accepted under accession No. NITE BP-771).

More preferably, in the culture step, killed cells of *Candida* are added.

The *Lactobacillus rhamnosus* KO1 strain of the eighth mode of the present invention was deposited with Patent Microorganisms Depositary, National Institute of Technology and Evaluation (Incorporated Administrative Agency) under accession No. NITE P-1065 by application as of Jan. 24, 2011.

Advantageous Effects of Invention

By the present invention, it is possible to provide a bacteriocin that is capable of being easily mass-produced, which bacteriocin has a wide antimicrobial spectrum and is less likely to produce resistant microorganisms; a composition for prophylaxis, amelioration and/or therapy of oral diseases comprising the bacteriocin (including pharmaceutically acceptable derivatives and the like thereof) as an effective component, a gene encoding the bacteriocin, a recombinant expression vector obtained by incorporation of the gene, a host cell comprising the recombinant expression vector, a transformant produced by transformation with the recombinant expression vector, a method for producing the bacteriocin, and a novel lactic acid bacterial strain that produces the bacteriocin, the *Lactobacillus rhamnosus* KO1 strain. Further, the bacteriocin of the present invention has high heat resistance, and the antimicrobial performance of the bacteriocin is maintained even under, for example, boiling conditions.

DESCRIPTION OF EMBODIMENTS

Figure 1:
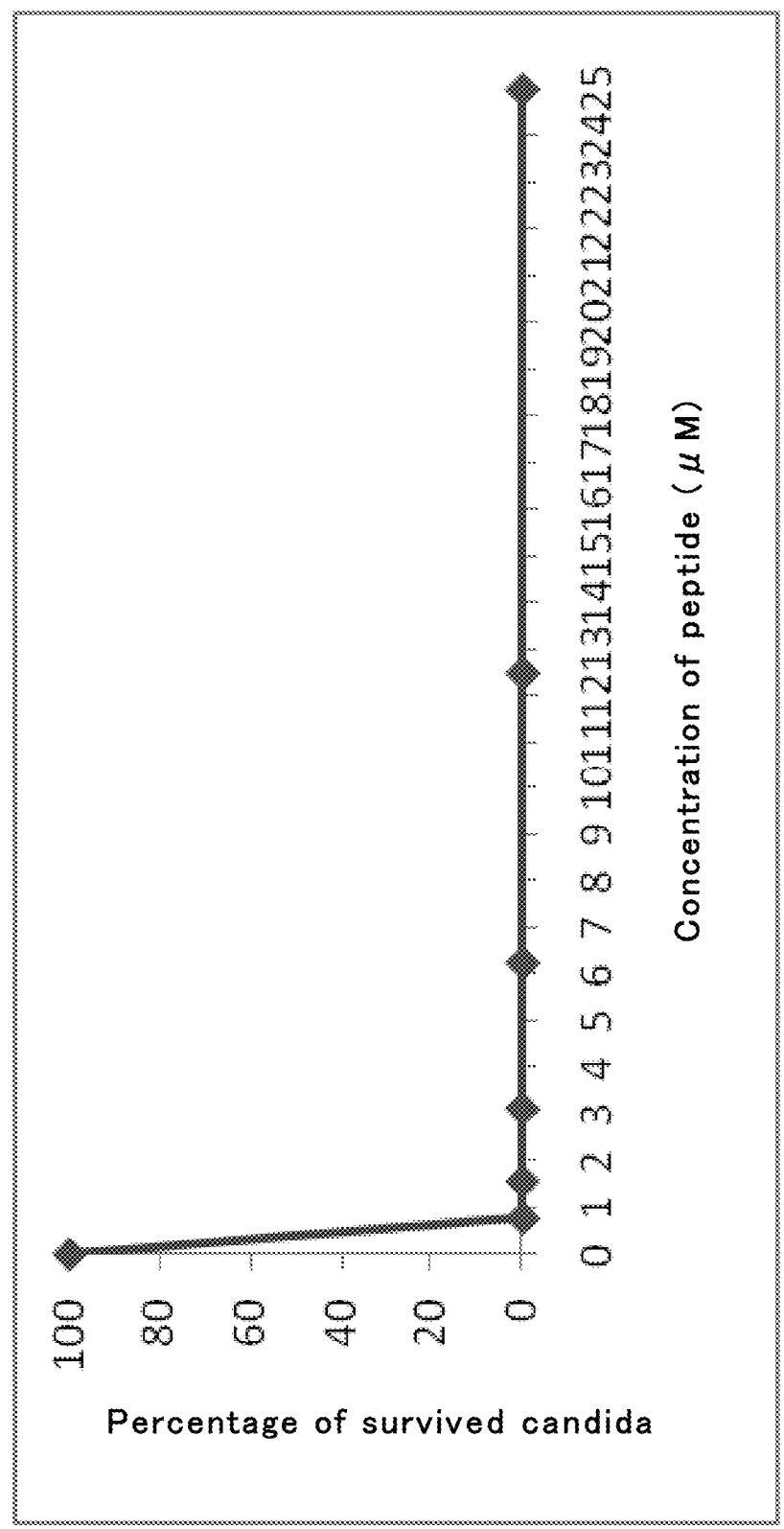
FIG. 1 is a diagram showing the antimicrobial activity of Kog1 (SEQ ID NO:1) at concentrations of 0.39 to 25 µM against the *Candida albicans* GDH18 strain observed in Example 2.

Embodiments of the present invention are described below in detail. In the present description, expressions such as "having", "comprising" and "containing" also include the meanings "consisting of" and "being constituted by".

(Bacteriocin)

The bacteriocin of the embodiment 1 of the present invention relates to a basic antimicrobial peptide having a specific amino acid sequence that produces a specific effect and has specific characteristics. Specific examples of the "bacteriocin" in the present description include the basic antimicrobial peptide having the amino acid sequence shown in SEQ ID NO: 1 (Kog1) and the basic antimicrobial peptide having the amino acid sequence shown in SEQ ID NO: 2 (Kog2). Further, the "bacteriocin" in the present description also includes basic antimicrobial peptides having the same amino acid sequence as the basic antimicrobial peptide having the amino acid sequence shown in SEQ ID NO: 1 or 2 except that one or several amino acids are deleted, substituted, inserted and/or added, which basic antimicrobial peptides provide antimicrobial activity and have isoelectric points of not less than 12. The term "several" means 2 to 8, preferably 2 to 6, more preferably 2 to 5, still more preferably 2 to 4.

In cases of a bacteriocin having the same amino acid sequence as the amino acid sequence of Kog1 or Kog2 except that one or several amino acids are deleted, substituted, inserted and/or added, which bacteriocin provides antimicrobial activity, the bacteriocin preferably has antimicrobial activity and basicity (isoelectric point) that are similar to antimicrobial activity and basicity of Kog1 or Kog2. The bacteriocin more preferably has antimicrobial activity against all of cariogenic bacteria, periodontal disease bacteria and *Candida*.

The bacteriocin of the embodiment 1 is optionally produced by a method using the *Lactobacillus rhamnosus* KO1 strain, KO3 strain or the like as described in detail in the embodiment 4 below. Alternatively, the bacteriocin of the embodiment 1 is produced by an artificial method conventionally used in the art, such as the peptide synthesis method, genetic engineering method or the like. The genetic engineering method is described in detail in the embodiment 3 below.

Examples of the peptide synthesis method include the liquid phase method and the solid phase method. The liquid phase method is a method wherein the reaction is carried out in the solution state and the product is isolated/purified from the reaction mixture, followed by using the product as an intermediate for the subsequent peptide elongation reaction. On the other hand, the solid phase method is a method wherein amino acids are bound to a solid carrier that is insoluble to the reaction solvent, and condensation reaction with these amino acids is sequentially carried out to elongate the peptide chain.

More specifically, in the peptide synthesis, an amino acid having a protected carboxyl group is bound to an amino acid having a protected amino group by dehydration condensation, to form a peptide bond. Subsequently, the amino-protecting group is removed, and the next amino acid having a protected amino group is bound to the free amino group. The step is repeated such that the peptide is sequentially elongated from the C-terminus to the N-terminus. In the dehydration condensation reaction, the carboxyl group is activated and allowed to react with the amino group to be bound. Examples of the method for the activation include the dicyclohexylcarbodiimide (DCC) method, active ester method, acid anhydride method and azide method. The method is appropriately selected in consideration of the reactivity, racemization and other side reactions. In order to prevent side reactions during the condensation reaction, protective groups are introduced to the amino group, carboxyl group and/or functional groups in the side chain of the amino acid. Preferably, these protective groups are stable under the conditions of the condensation reaction, and is capable of being quickly removed when necessary. Further, preferably, the protective group for the amino group and the protective group for the carboxyl group are capable of being removed selectively therebetween.

Examples of the protective group for the amino group include benzyloxycarbonyl (Bz), t-butyloxycarbonyl (Boc), p-biphenylisopropyloxycarbonyl and 9-fluorenylmethyloxycarbonyl (Fmoc). Examples of the protective group for the carboxyl group include groups capable of forming an alkyl ester, benzyl ester or the like.

However, in the solid phase method, the carboxyl group at the C-terminus is bound to a carrier such as a chlorotrityl resin, chloromethyl resin, oxymethyl resin or p-alkoxybenzylalcohol resin, so that the condensation reaction is preferably carried out in the presence of a condensing agent such as carbodiimide, or using an N-protected amino acid activated ester or a peptide activated ester. After completion of the condensation reaction, the protective group is removed. In the solid phase method, the bond between the C-terminus of the peptide and the resin is also cleaved. Thereafter, the chemically synthesized peptide is optionally subjected to, for example, purification/analysis by ion-exchange chromatography, high-performance liquid chromatography (HPLC), reversed phase chromatography, affinity chromatography, Edman degradation method, gas chromatography mass spectrometry (GC-MS) and/or the like.

It is possible to use the bacteriocin of the embodiment 1 produced by such a peptide synthesis method or by the later-described method using the genetic engineering method and the *Lactobacillus rhamnosus* KO1 strain or KO3 strain, or a pharmaceutically acceptable derivative of the bacteriocin, as an effective component of the composition for prophylaxis, amelioration and/or therapy of oral diseases of the embodiment 2 described below.

(Composition for Prophylaxis, Amelioration and/or Therapy of Oral Diseases)

The embodiment 2 of the present invention is a composition for prophylaxis, amelioration and/or therapy of oral diseases, which composition comprises the bacteriocin of the embodiment 1 described above or a pharmaceutically acceptable derivative or the like of the bacteriocin as an effective component Since the composition for prophylaxis, amelioration and/or therapy of oral diseases of the embodiment 2 comprises the bacteriocin of the embodiment 1 or a pharmaceutically acceptable derivative or the like of the bacteriocin as an effective component, the composition has similar characteristics.

Briefly, the amino acid sequences of the bacteriocins Kog1 and Kog2 described in the embodiment 1, and characteristics of the amino acid sequences are as follows. The amino acid sequences characteristically have basic amino acids and hydrophobic amino acids at high ratios. Since such characteristics are similar to characteristics of antimicrobial peptides derived from mammals, resistant microorganisms are less likely to be produced. Further, since the isoelectric point is not less than 12 and the antimicrobial peptide has high basicity, cytotoxicity of the peptide is low. Further, as described in Examples below, the peptide has excellent antimicrobial activity. For details of such effects of Kog1 or Kog2, see Examples below.

In the present description, the term "oral diseases" means diseases in the oral cavity caused by cariogenic bacteria, periodontal disease bacteria, *Candida* and/or the like. Specific examples of the oral diseases include dental caries (bad tooth), gingivitis, periodontitis, glossitis, thrush and angular cheilitis.

Examples of the cariogenic bacteria include *Streptococcus mutans* and *Streptococcus sobrinus*. Examples of the periodontal disease bacteria include Aggregatibacter *actinomycetemcomitans* Hudoe001, *Porphyromonas gingivalis, Prevotella intermedia, Treponema denticola, Tannerella forsythensis. Actinobacillus actinomycetemcomitans* and *Fusobacterium nucleatum*. Examples of the *Candida* include *Candida albicans, Candida glabrata* and *Candida tropicalis*.

In the present description, the term "composition for prophylaxis, amelioration and/or therapy of oral diseases" preferably means a composition that acts as a growth inhibitor of cariogenic bacteria, periodontal disease bacteria and/or *Candida*. Specific examples of the composition include foods, pharmaceuticals and oral compositions that are capable of suppressing the growth of cariogenic bacteria, periodontal disease bacteria and/or *Candida*.

More specifically, examples of the foods include health foods, supplements, specified health foods, milk beverages, yogurts and cheeses that are intended for prophylaxis/amelioration of dental caries, periodontitis, oral infections and the like. Examples of the pharmaceuticals include liquids, pills, granules, subtle granules, powders, tablets, capsules, oral sprays and troches. The administration mode is preferably oral administration. Examples of the oral compositions include mouth-rinsing agents, mouth washes, toothpastes, tooth powders, tooth liquids, oral ointments, gels, pills, granules, subtle granules, gummy jellies, troches, tablets, capsules, candies and chewing gums.

The composition for prophylaxis, amelioration and/or therapy of oral diseases of the embodiment 2 is optionally combined with other pharmaceutically acceptable compositions for preparing various foods, pharmaceuticals, oral compositions and the like. Further, the bacteriocin and the composition are optionally used in the form of a derivative or salt.

Examples of the derivative include peptide derivatives such as partial substitution products and addition compounds of bacteriocin. Specific examples of the derivative include derivatives produced by amidation or acylation of a carboxyl group. Examples of the form of the salt include inorganic acid salts such as hydrochloric acid salt, nitric acid salt and hydrobromic acid salt; and organic acid salts such as p-toluenesulfonic acid salt, methanesulfonic acid salt, fumaric acid salt, succinic acid salt and lactic acid salt.

Further, in the foods, pharmaceuticals and oral compositions, it is possible to appropriately adjust the content and the daily dose of the bacteriocin of the embodiment 1 as an effective component depending on the type of the composition.

(Gene)

The embodiment 3 of the present invention relates to a gene that encodes the bacteriocin of the embodiment 1. Specific examples of the gene include genes and polynucleotides having the base sequence shown in SEQ ID NO: 3 (Kog1) or SEQ ID NO: 4 (Kog2) (and/or the complementary strand thereof).

The skilled person in the art is able to separate, purify and extract DNA of such a gene having the base sequence shown in SEQ ID NO: 3 (Kog1) or SEQ ID NO: 4 (Kog2) from the *Lactobacillus rhamnosus* KO1 strain or KO3 strain using a conventional method. Another possible example of the method is artificial synthesis of the DNA using a DNA synthesis kit or the like.

(Recombinant Expression Vector)

It is possible to use the gene sequence that was separated and purified, or produced by DNA synthesis using a kit or the like, for a recombinant expression vector to be used for producing the bacteriocin of the embodiment 1 by the genetic engineering method. The embodiment 4 relates to a recombinant expression vector obtained by incorporation of the gene of the embodiment 3. Examples of the method of recombination include an arbitrary method used by the skilled person. In the method of construction of the recombinant expression vector, synthesis of a gene having the base sequence shown in SEQ ID NO: 3 (Kog1) or SEQ ID NO: 4 (Kog2) is first carried out. Subsequently, a recombinant expression vector comprising a gene construct for expression, which construct comprises the synthesized gene and various regulatory elements for expression of the gene in the host cell (a promoter, ribosome binding site, terminator, enhancer and/or various cis-elements for regulating the expression level), is constructed depending on the host cell.

(Host Cell, Transformant)

The thus constructed recombinant expression vector is introduced to a predetermined host cell such that expression of the gene is possible. Examples of the method of introduction include an arbitrary method used by a skilled person. The embodiment 5 relates to a host cell comprising the recombinant expression vector. The host cell is preferably a bacterium. Examples of the host cell include lactic acid bacteria, *E. coli* and yeasts. The embodiment 6 relates to a transformant produced by transformation with the recombinant expression vector. That is, examples of the transformant include a transformed cell produced by transformation of the host cell having the recombinant expression vector of the embodiment 5. The transformant is preferably a bacterium. Examples of the transformant similarly include lactic acid bacteria, *E. coli* and yeasts. The bacteria are cultured under predetermined conditions. The above process allows expression and production of the bacteriocin of the embodiment 1 in the host cell (bacterium), and simple and large-scale extraction and purification of the bacteriocin. For details of the production method, see the later-described embodiment 7, wherein the lactic acid bacterium *Lactobacillus rhamnosus* is cultured by almost the same method.

(Method for Producing Bacteriocin)

The embodiment 7 of the present invention relates to a method for producing the bacteriocin of the embodiment 1 using *Lactobacillus rhamnosus*.

More specifically, the production method comprises the step of culturing *Lactobacillus rhamnosus* and the step of extracting the bacteriocin of the embodiment 1 from a bacterial cell culture obtained by the culture step. The *Lactobacillus rhamnosus* is preferably the *Lactobacillus rhamnosus* KO3 strain and/or the novel lactic acid bacterial strain, the *Lactobacillus rhamnosus* KO1 strain.

For example, the *Lactobacillus rhamnosus* KO1 strain and KO3 strain are inoculated to MRS medium sterilized at 121° C. for 20 minutes or the like, and precultured at 37° C. for 48 hours in air, followed by washing with distilled water, ultrapure water, buffer or the like and then centrifugation for collection of the cells, to obtain bacterial cells.

Since the *Lactobacillus rhamnosus* KO1 strain and KO3 strain produce Kog1 and Kog2, it is suggested that Kog1 and Kog2 are produced as long as the bacterial strain belongs to the *Lactobacillus rhamnosus* species. Thus, large-scale culture of a bacterial strain belonging to the *Lactobacillus rhamnosus* species and use of a conventional method for protein extraction in the art (for example, cell homogenization) enable simple and mass production of the Kog1 and Kog2 peptides.

In the culturing step, it is possible to use various media such as fruit juice media, vegetable juice media, milk media, nonfat dry milk media, media containing a milk component, and semi synthetic media containing no milk component. Specific examples of the media include reconstituted skim milk media prepared by reconstituting and heat-sterilizing a skim milk; nonfat dry milk media supplemented with an yeast extract; MRS media; and GAM media.

The culture method is not limited as long as the culture is, for example, static culture, neutralizing culture at a constant pH, rotation culture or continuous culture that is carried out under conditions where the *Lactobacillus rhamnosus* grows well. Details of the bacteriological properties of the *Lactobacillus rhamnosus* KO3 strain are almost the same as the details of the bacteriological properties of the novel lactic acid bacterial strain, the *Lactobacillus rhamnosus* KO1 strain, described below in the embodiment 8.

Addition of killed cells of *Candida* in the culture step increases the amounts of Kog1 and Kog2 obtained, which is preferred (see Example 6).

(*Lactobacillus rhamnosus* KO1 Strain)

The *Lactobacillus rhamnosus* KO1 strain (deposited with Patent Microorganisms Depositary, National Institute of Technology and Evaluation under accession No. NITE P-1065 by application as of Jan. 24, 2011) is a lactic acid bacterial strain newly separated from the oral cavity of human and identified by the present inventor. Similarly to the *Lactobacillus rhamnosus* KO3 strain, the *Lactobacillus rhamnosus* KO1 strain is classified into the *Lactobacillus rhamnosus* species that produces Kog1 and Kog2, but the *Lactobacillus rhamnosus* KO1 strain is a novel lactic acid bacterial strain wherein the expression levels of various proteins and the genomic information are different.

The *Lactobacillus rhamnosus* KO1 strain was identified as the *Lactobacillus rhamnosus* species since the base sequence of 16S rRNA in the KO1 strain showed a homology of 100% between 1443/1443 with the base sequence in the *Lactobacillus rhamnosus* strain IDCC3201, and the KO1 strain exhibited appearance of a Gram-positive *bacillus* under the microscope after Gram staining. The *Lactobacillus rhamnosus* KO1 strain has the bacteriological properties of being a Gram-positive lactic acid *bacillus*; being capable of homolactic acid fermentation; being catalase-negative; having no spore-forming ability; being capable of growing under aerobic conditions; and forming extracellular polysaccharides.

As described above in the embodiment 7, culturing of the novel lactic acid bacterial strain of the embodiment 8, the *Lactobacillus rhamnosus* KO1 strain, enables simple and mass extraction of the basic antimicrobial peptides of the embodiment 1, that is, Kog1 and Kog2, from a bacterial culture obtained by the culture, so that the strain is effective.

EXAMPLES

The present invention is described below in more detail by way of Examples. However, the present invention is not limited by Examples.

Preparation Example

In the present Preparation Example, methods for preparation and culture of test strains are described.

As the *Candida*, cariogenic bacteria and periodontal disease bacteria, the *Candida albicans* GDH18 strain, *Streptococcus sobrinus* B-13 strain, *Streptococcus mutans* NCTC10449 strain, *Streptococcus mutans* Ingbritt strain, *Porphyromonas gingivalis* Hudoi001 strain and *Aggregatibacter actinomycetemcomitans* Hudoe001 strain were used. The test strains were provided from Faculty of Dentistry, Hiroshima University, Japan, and Hiroshima University Dental Hospital.

The *Candida albicans* GDH18 strain was precultured using SD medium (Difco) at 37° C. for 24 hours under aerobic conditions. The *Streptococcus sobrinus* B-13 strain, *Streptococcus mutans* NCTC10449 strain and *Streptococcus mutans* Ingbritt strain were precultured using TSB medium (Difco) supplemented with 5% yeast extract (Difco) at 37° C. for 24 hours under aerobic conditions. The *Porphyromonas gingivalis* Hudoi001 strain and *Aggregatibacter actinomycetemcomitans* Hudoe001 strain were precultured using BHI medium (Difco) supplemented with hemin (5 mg/L) and vitamin K3 (1 mg/L) at 37° C. for 96 hours under anaerobic conditions with Anaero Pack System (Mitsubishi Gas Chemical Company, Inc.).

After the culture, the cells of the *Candida*, cariogenic bacteria and periodontal disease bacteria were collected by centrifugation at 1000×g, and washed twice with 1 mM phosphate buffer (pH 6.8). The cells were then suspended such that the final concentration was $1 \times 10^8$ cfu/ml or $1 \times 10^7$ cells/m. For suspension of the *Streptococcus* strains, ultrasonic treatment was also carried out.

Example 1

The Example 1 relates to synthesis of Kog1 and Kog2.

First, for confirming the function as bacteriocin, Kog1 having the amino acid sequence shown in SEQ ID NO: 1 and Kog2 having the amino acid sequence shown in SEQ ID NO: 2 were synthesized by the tea-bag method (method by Helmerhorst and others (1999)) using 9-fluorenylmethyloxycarbonyl as a protective group and p-benzyloxybenzyl alcohol as a resin. After completion of a basic antimicrobial peptide, cleavage from the resin and deprotection of the side chain were carried out using the mixture of 5% thioanisole, 5% phenol, 5% purified water and 85% trifluoroacetic acid.

Based on measurement of the isoelectric point (pI) and molecular weight (MW) of each of the synthesized Kog1 and Kog2, Kog1 had a pI of 12.90 and a MW of 5485.5, and Kog2 had a pI of 12.38 and a MW of 4686.6. Among antimicrobial peptides, hBD2 (human P-defensin-2 (see Eur J., 2002, Oral Sci. (109), 121-124)) is well known as a basic antimicrobial peptide, and has an isoelectric point of about 10. However, the isoelectric points of Kog1 and Kog2 of the embodiment 2 were higher than the isoelectric point of hBD2, and more similar to the isoelectric points of antimicrobial peptides derived from mammals. Thus, Kog1 and Kog2 were confirmed to have less cytotoxicity.

Purification and analysis of the purity of each synthesized peptide were carried out by high-performance liquid chromatography and reversed phase chromatography. The molecular weight was investigated with a mass spectrometer (MALDI-TOF).

Example 2

Example 2 relates to analysis of the antimicrobial activities of Kog1 and Kog2 against the *Candida albicans* GDH18 strain.

Evaluation of the antimicrobial activity was carried out by the method by Edgerton and others (1998) with some modifications. With 20 mL of 1 mM phosphate buffer containing 0 to 25 µM Kog1 or Kog2 synthesized in Example 1, 20 µl of the suspension of the *Candida albicans* GDH18 strain cultured and prepared by the method described in the above Preparation Example was mixed, and the resulting mixture was incubated at 37° C. for 90 minutes with shaking. As a control, 20 ml of 1 mM phosphate buffer alone was used. The reaction was stopped by addition of 360 ml of YNB medium (Difco), and the number of colonies formed (colony forming units; CFUs) was counted together with the number of colonies in the control, to determine the percentage of living bacterial cells. That is, the equation of: (CFUs of suspension containing Kog1 or Kog2/CFU ml$^{-1}$ of control suspension)×100 was used to calculate the percentage.

Figure 2:
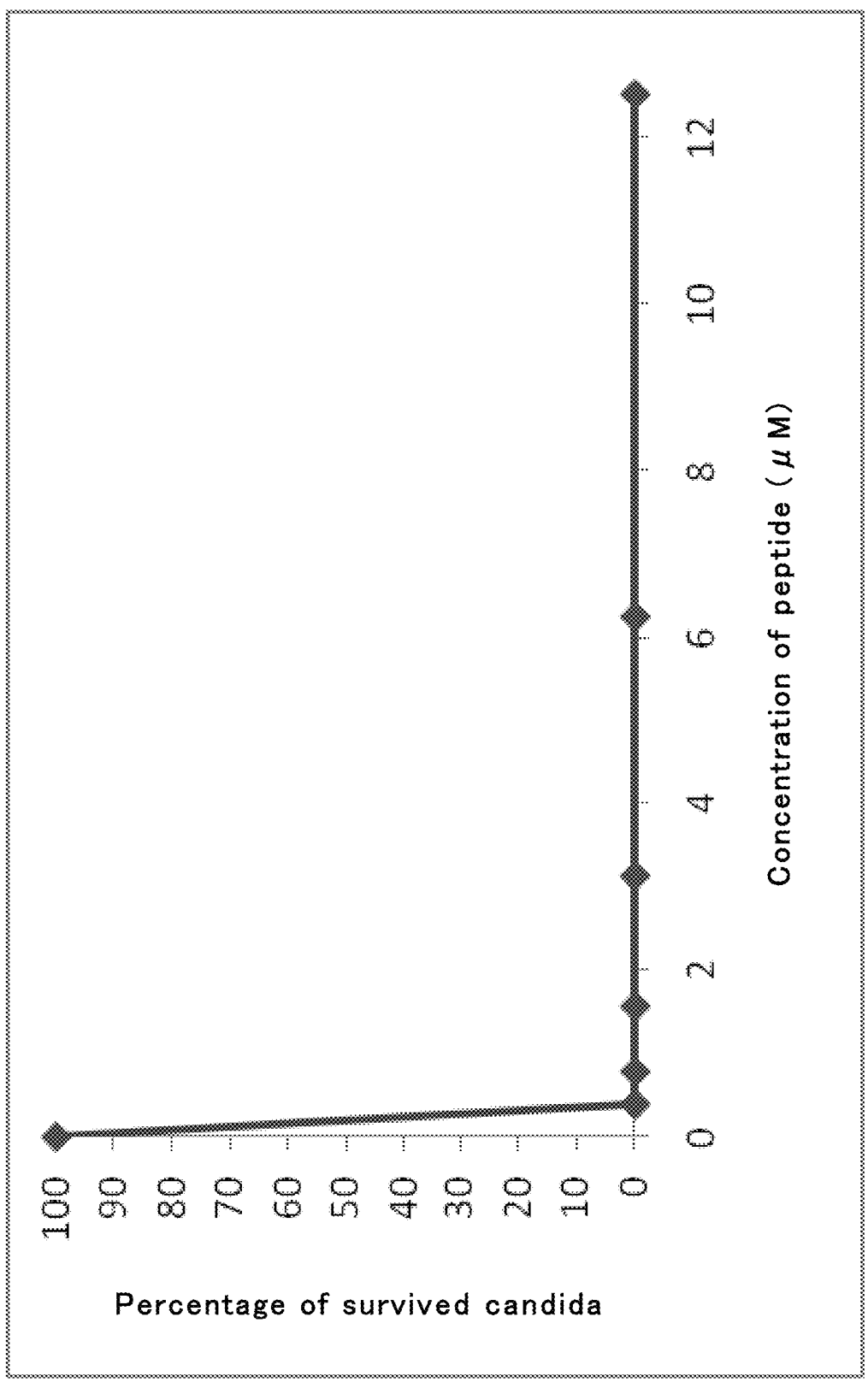
FIG. 2 is a diagram showing the antimicrobial activity of Kog2 (SEQ ID NO:2) at concentrations of 0.39 to 12 µM against the *Candida albicans* GDH18 strain observed in Example 2.

FIG. 1 is a diagram showing the antimicrobial activity of Kog1 at concentrations of 0.39 to 25 µM against the *Candida albicans* GDH18 strain observed in Example 2. FIG. 2 is a diagram showing the antimicrobial activity of Kog2 at concentrations of 0.39 to 12 µM against the *Candida albicans* GDH18 strain observed in Example 2. As shown in FIG. 1 and FIG. 2, 100% of the *Candida albicans* GDH18 strain was killed at a peptide concentration of 0.39 µM in both Kog1 and Kog2.

By the same method and under the same conditions, amphotericin B, which is an antifungal agent; lactoferricin B, which is an antimicrobial peptide derived from milk (having the amino acid sequence shown in SEQ ID NO: 5); histatin 5, which is an antimicrobial peptide derived from human saliva (having the amino acid sequence shown in SEQ ID NO: 6); and JH8194, which is an antimicrobial peptide of JP 3472821 B (having the amino acid sequence shown in SEQ ID NO: 7); were subjected to measurement of the antimicrobial activity. As a result, the above agent/peptides killed 100% of the strain at concentrations of 5 µM, 5 µM, 100 µM and 2.5 µM, respectively. Synthesis of the peptides was carried out by the tea-bag method as in Example 1.

From the above results, it was proved that the antimicrobial peptides Kog1 and Kog2 are capable of killing *Candida* even in cases where the peptides are used at a lower concentration, that is, in a smaller amount, compared to any of the above antifungal agent and antimicrobial peptides.

Example 3

Example 3 relates to analysis of the antimicrobial activities of Kog1 and Kog2 against the *Streptococcus sobrinus* B-13 strain. More specifically, Example 3 is an example wherein the antimicrobial activities of Kog1 and Kog2 were compared with the antimicrobial activities of hBD2 and lysozyme protein (Lysozyme).

The *Streptococcus sobrinus* B-13 strain was preliminarily cultured and prepared by the method described in the Preparation Example. Evaluation of the antimicrobial activity was carried out by the same method as in the above Example 2. The evaluation was carried out for cases where the concentration of each antimicrobial peptide was 0 to 100 µM.

Figure 3:
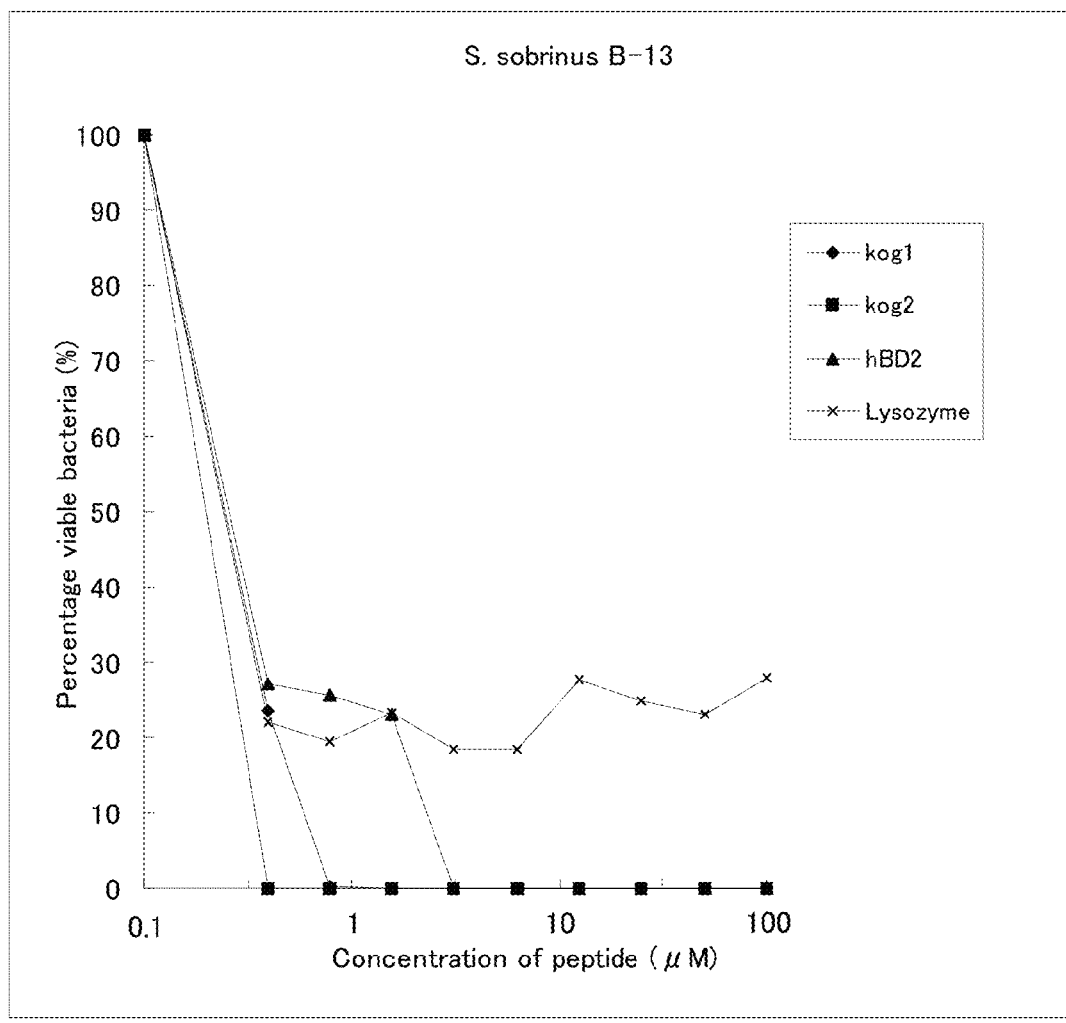
FIG. 3 is a diagram showing the antimicrobial activities of Kog1 (SEQ ID NO:1). Kog2 (SEQ ID NO:2), and antimicrobial peptides hBD2 (human β-defensin-2) and lysozyme against the *Streptococcus sobrinus* B-13 strain observed in Example 3.

FIG. 3 is a diagram showing the antimicrobial activities of Kog1, Kog2 and the other antimicrobial peptides against the *Streptococcus sobrinus* B-13 strain observed in Example 3. The peptide concentrations are plotted on a logarithmic scale on the abscissa ("Concentration of peptide") in FIG. 3. As shown in FIG. 3, hBD2 killed 100% of the *Streptococcus sobrinus* B-13 strain at a peptide concentration of 3.125 µM. Lysozyme protein failed to completely kill the *Streptococcus sobrinus* B-13 strain. On the other hand, Kog1 and Kog2 killed 100% of the *Streptococcus sobrinus* B-13 strain at concentrations of 1.56 µM and 0.39 µM, respectively. Therefore, it was proved that Kog1 and Kog2 are also capable of killing the *Streptococcus sobrinus* B-13 strain even in cases where the peptides are used at low concentration.

Example 4

Example 4 relates to analysis of the antimicrobial activities of Kog1 and Kog2 against the *Streptococcus mutans* bacterium. More specifically, similarly to the above Example 3, Example 4 is an example wherein the antimicrobial activities of Kog1 and Kog2 were compared with the antimicrobial activities of hBD2 and lysozyme protein (Lysozyme).

The *Streptococcus mutans* NCTC10449 strain and the *Streptococcus mutans* Ingbritt strain were preliminarily cultured and prepared by the method described in the Preparation Example. Evaluation and comparison of the antimicrobial activity were carried out by the same method as in the above Example 3. The evaluation and comparison were carried out for cases where the antimicrobial peptide concentration was 0 to 100 µM for both *Streptococcus mutans* strains.

Figure 4:
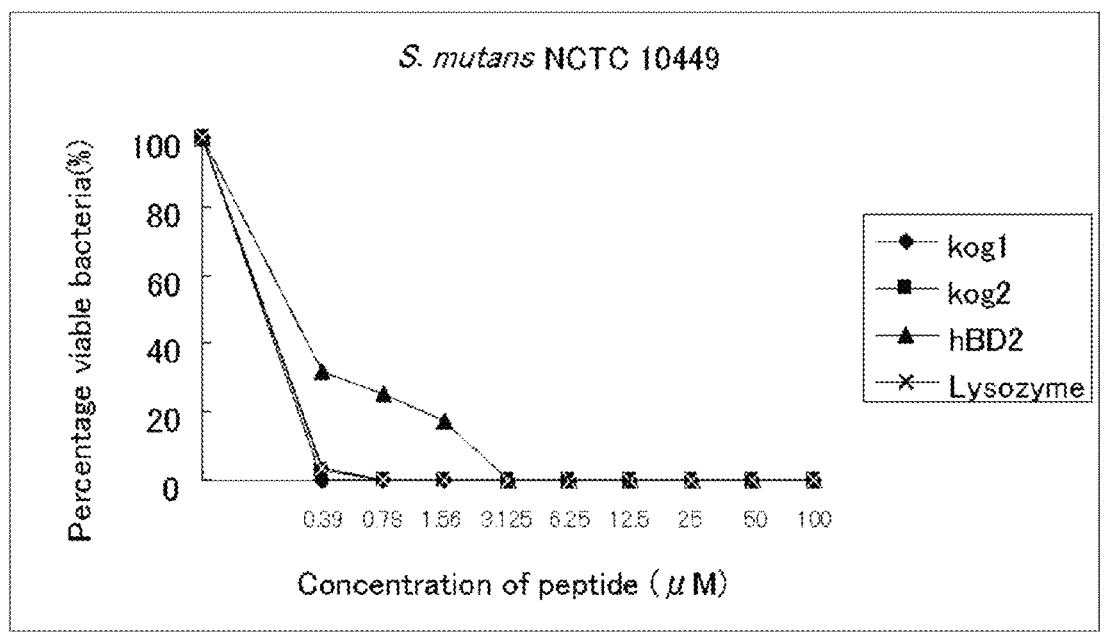
FIG. 4 is a diagram showing the antimicrobial activities of Kog1 (SEQ ID NO:1), Kog2 (SEQ ID NO:2), hBD2, and lysozyme against the *Streptococcus mutans* NCTC10449 strain observed in Example 4.
Figure 5:
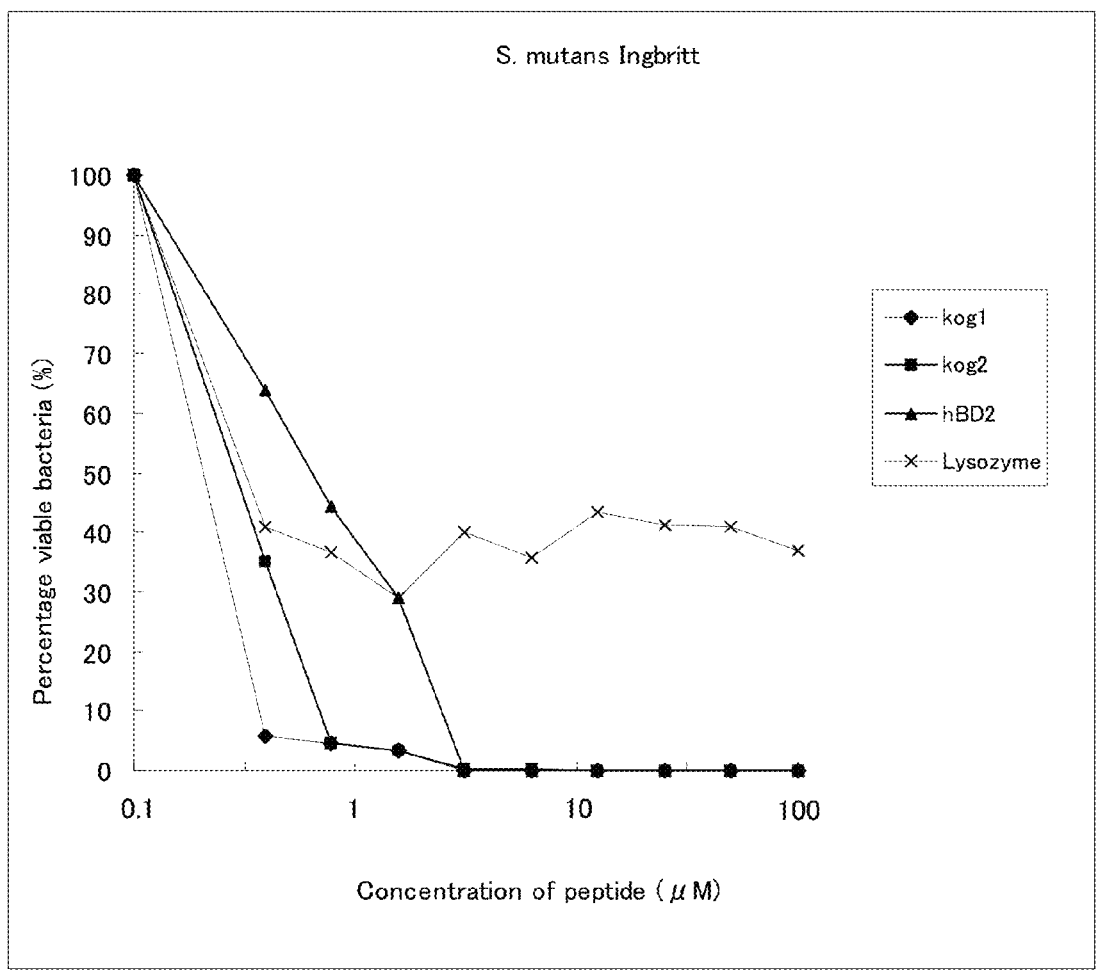
FIG. 5 is a diagram showing the antimicrobial activities of Kog1 (SEQ ID NO:1), Kog2 (SEQ ID NO:2), hBD2, and lysozyme against the *Streptococcus mutans* Ingbritt strain observed in Example 4.

FIG. 4 is a diagram showing the antimicrobial activities of Kog1, Kog2 and the other antimicrobial peptides against the *Streptococcus mutans* NCTC10449 strain observed in Example 4. FIG. 5 is a diagram showing the antimicrobial activities of Kog1, Kog2 and the other antimicrobial peptides against the *Streptococcus mutans* Ingbritt strain observed in Example 4. The peptide concentrations are plotted on a logarithmic scale on the abscissa ("Concentration of peptide") in each of FIG. 4 and FIG. 5. As shown in FIG. 4 and FIG. 5, Kog1 and Kog2 were evaluated as being capable of killing a larger amount of *Streptococcus mutans* even at relatively low peptide concentration compared to the other antimicrobial peptides.

Further, although not shown in the figures, Kog1 and Kog2 were also evaluated as being capable of exerting antimicrobial activity against the *Porphyromonas gingivalis* Hudoi001 strain. Such a result is also suggested by the fact evaluated and described in Examples in Patent Literature 1 that the *Lactobacillus rhamnosus* KO3 strain, which was discovered by the present inventor, also exerts antimicrobial activity against the *Porphyromonas gingivalis* Hudoi001 strain. That is, it is assumed that, in Examples described in Patent Literature 1, the *Lactobacillus rhamnosus* KO3 strain expressed Kog1 and Kog2, and the expressed Kog1 and Kog2 exerted antimicrobial activity against the *Porphyromonas gingivalis* Hudoi001 strain. In view of the above facts, it is assumed that Kog1 and Kog2 exert similar antimicrobial activity also against other strains of *Porphyromonas gingivalis* (periodontal disease bacteria and the like).

Example 5

Further, the present inventor also analyzed antimicrobial activity against another periodontal disease bacterium.

Example 5 relates to analysis of antimicrobial activities of the bacteriocins Kog1 and Kog2 against the periodontal disease bacterium *Aggregatibacter actinomycetemcomitans* Hudoe001 strain. More specifically, Example 5 shows an example wherein the antimicrobial activities of Kog1 and Kog2 were compared again with the antimicrobial activities of hBD2 and histatin 5, and further with the antimicrobial activities of lactoferricin B and lactoferrcin H (human-derived lactoferricin).

The *Aggregatibacter actinomycetemcomitans* Hudoe001 strain was preliminarily cultured and prepared by the method described in the Preparation Example. Evaluation and comparison of the antimicrobial activity were carried out by the same method as in the above Example 3. The evaluation and comparison were carried out for cases where the concentration of each antimicrobial peptide was 0 to 50 µM.

Figure 6:
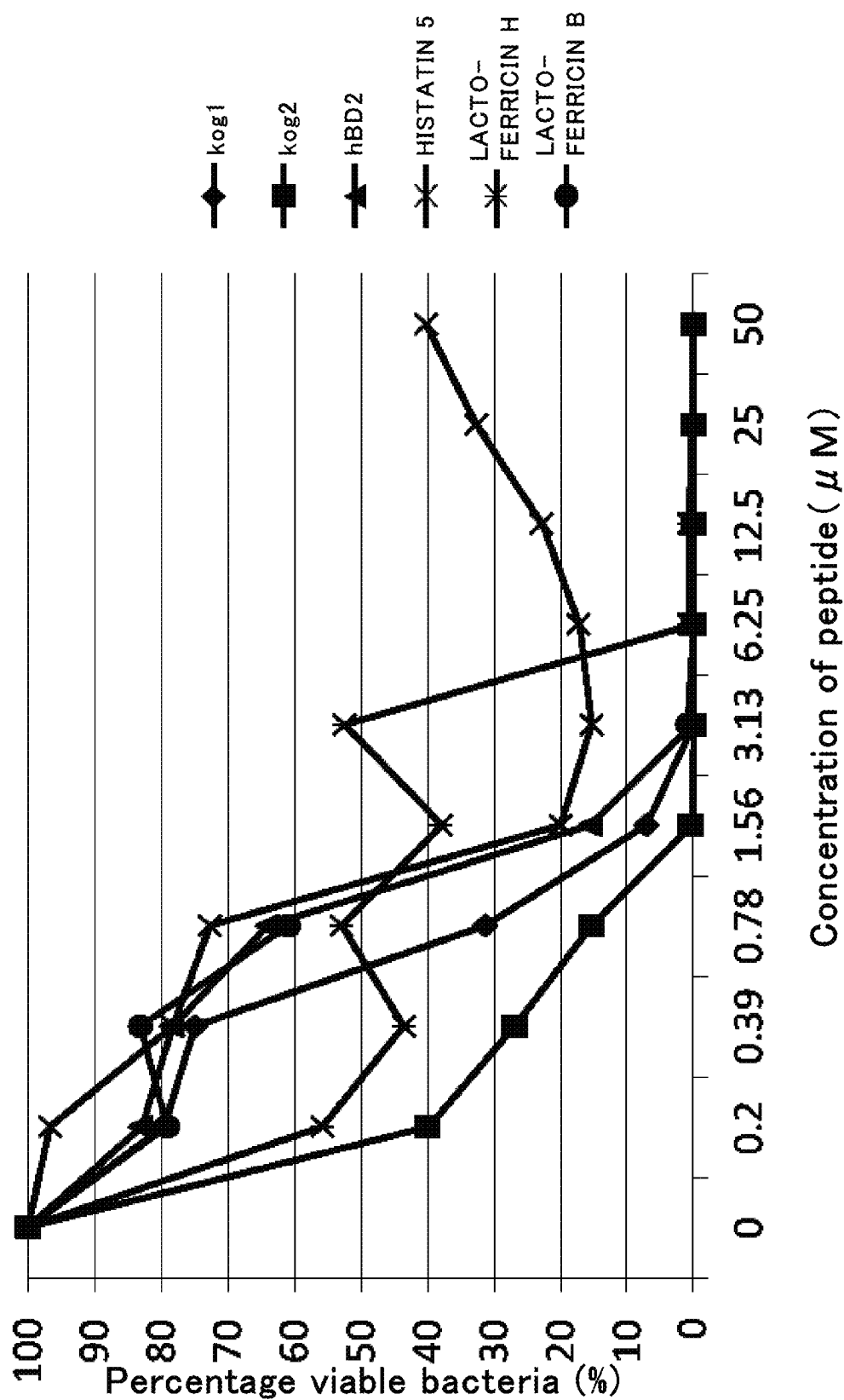
FIG. 6 is a diagram showing the antimicrobial activities of Kog1 (SEQ ID NO:1), Kog2 (SEQ ID NO:2), and antimicrobial peptides histatin 5, lactoferricin H, and lactoferricin B against the *Aggregatibacter actinomycetemcomitans* Hudoe001 strain observed in Example 5.

FIG. 6 is a diagram showing the antimicrobial activities of Kog1, Kog2 and the other antimicrobial peptides against the *Aggregatibacter actinomycetemcomitans* Hudoe001 strain observed in Example 5. The peptide concentrations are plotted on a logarithmic scale on the abscissa ("Concentration of peptide") in FIG. 6. As shown in FIG. 6, Kog1 and Kog2 killed 100% of the periodontal disease bacterium *Aggregatibacter actinomycetemcomitans* Hudoe001 strain at peptide concentrations of 3.13 µM and 1.56 µM, respectively. The observed antimicrobial activities are equivalent to or higher than the antimicrobial activities of lactoferricin B and hBD2.

Example 6

Example 6 relates to culture of the *Lactobacillus rhamnosus* KO1 strain which was carried out while killed cells of *Candida* were added. More specifically, the *Lactobacillus rhamnosus* KO1 strain was cultured in the absence and in the presence of killed cells of the *Candida albicans* GDH18 strain, and the expression levels of Kog1 and Kog2 were measured by the DNA microarray system.

First, 20 µl of a *Lactobacillus rhamnosus* KO1 strain suspension was inoculated to 5 ml of MRS medium containing 0, 2, 4 or 6 µg of killed cells of the *Candida albicans* GDH18 strain, and the resulting culture liquid was incubated at 37° C. for 48 hours. Immediately thereafter, the bacterial cells were suspended in 100 ml of RNAprotect reagent (Qiagen) and 900 ml of Rifampin (25 mg/ml, in methanol) (Sigma-Aldrich). Subsequently, the resulting suspension was vortexed for 15 minutes, and then incubated at room temperature for 10 minutes. After the treatments, the bacterial cells were collected by centrifugation, and the supernatant was discarded, followed by storing the obtained pellet at −20° C. From the stored pellet, purification was performed using an RNA extraction kit. After such pretreatment, statistical analysis of microarray data was carried out using NimbleGen software for microarray analysis.

Figure 7:
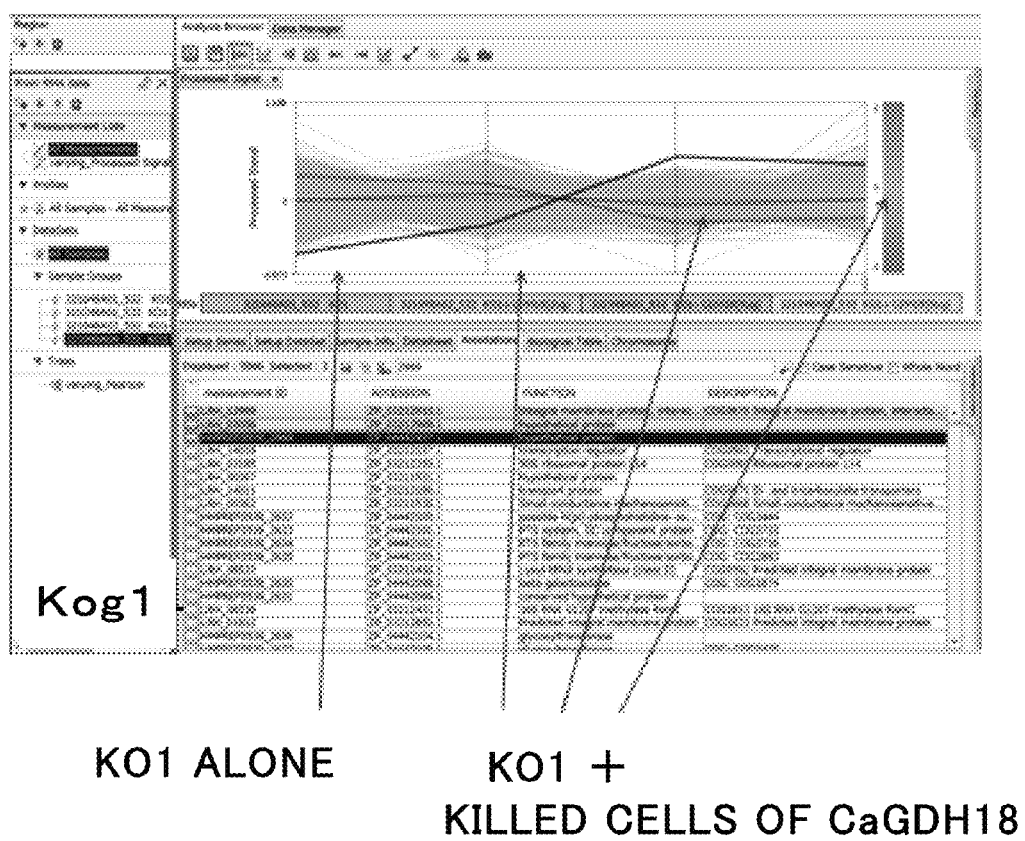
FIG. 7 is a diagram showing the expression level of Kog1 (SEQ ID NO:1) in the *Lactobacillus rhamnosus* KO1 strain after addition of killed cells of *Candida* as observed by DNA microarray in Example 6.
Figure 8:
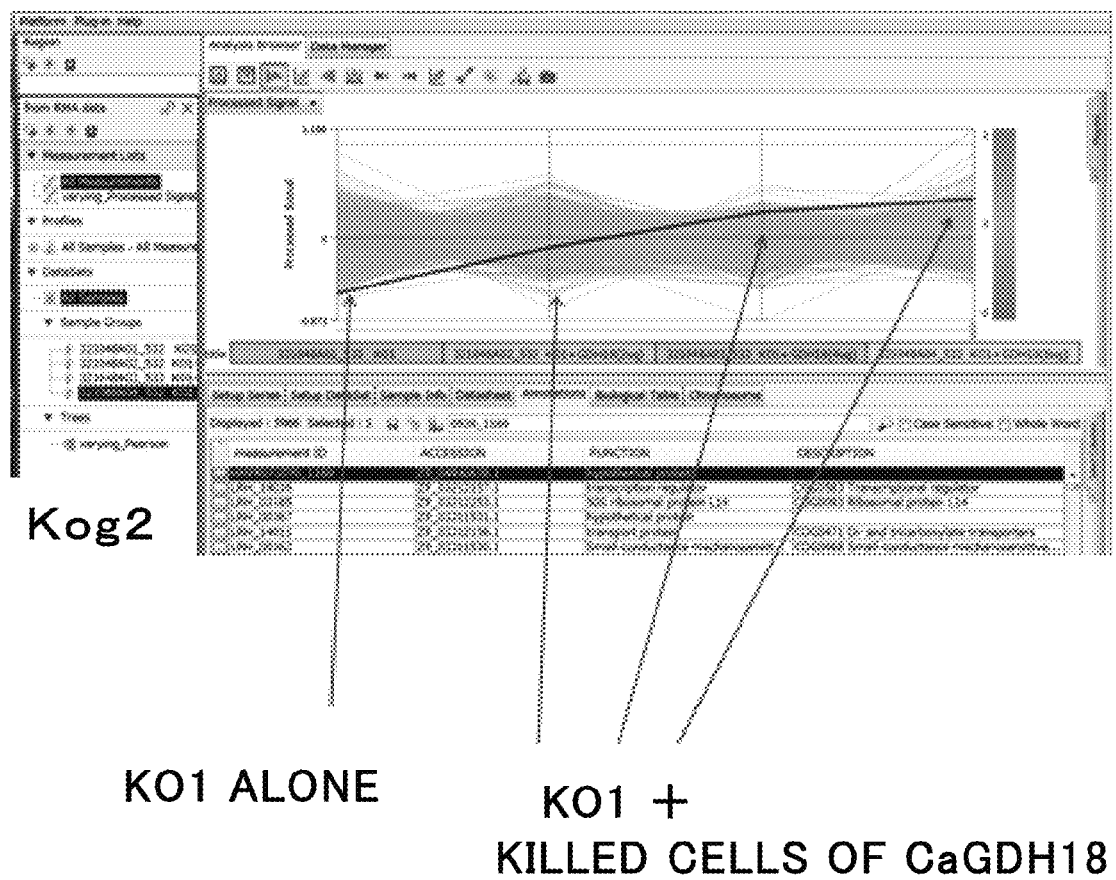
FIG. 8 is a diagram showing the expression level of Kog2 (SEQ ID NO:2) in the *Lactobacillus rhamnosus* KO1 strain after addition of killed cells of *Candida* as observed by DNA microarray in Example 6.

FIG. 7 is a diagram showing the expression level of Kog1 in the *Lactobacillus rhamnosus* KO1 strain after addition of killed cells of *Candida* as observed by DNA microarray in Example 6. FIG. 8 is a diagram showing the expression level of Kog2 in the *Lactobacillus rhamnosus* KO1 strain after addition of killed cells of *Candida* as observed by DNA microarray in Example 6. As shown in FIG. 7 and FIG. 8, in contrast to the case shown in the left end where culture was carried out only with the KO1 strain, culturing of the strain in the coexistence of killed cells of *Candida* (CaGDH18) resulted in increases in the expression levels of both Kog1 and Kog2 depending on the amount of killed cells (2, 4 and 6 µg from the left).

From the above results of Examples, it was proved that culturing of the *Lactobacillus rhamnosus* KO1 strain, which is a novel lactic acid bacterial strain, or the *Lactobacillus rhamnosus* KO3 strain, which similarly produces Kog1 and Kog2, enables simple and mass production of bacteriocins Kog1 and Kog2, which have wide antimicrobial spectra (cariogenic bacteria, periodontal disease bacteria and *Candida*) and are less likely to produce resistant microorganisms, while having isoelectric points of not less than 12. Further, it is suggested that simple and mass production of the bacteriocins Kog1 and Kog2 is also possible in other strains of *Lactobacillus rhamnosus*. Further, from the above results, it is evident to the skilled person in the art that culturing of a bacterium such as a lactic acid bacterium or *E. coli* produced by transformation with a recombinant expression vector obtained by incorporation of a gene encoding the bacteriocin Kog1 or Kog2 also enables simple and mass production of the bacteriocin Kog1 or Kog2, which has excellent antimicrobial activity.

Example 7

In Example 7, the wide antimicrobial spectra of the bacteriocins Kog1 and Kog2 and the unlikeliness of production of resistant microorganisms due to the basic isoelectric points of the bacteriocins Kog1 and Kog2, which were demonstrated in Examples 1 to 6, were studied. The present inventor predicted that the bacteriocins Kog1 and Kog2 inactivate LPS of Gram-negative bacteria such as periodontal disease bacteria, and analyzed the relationship between LPS and the bacteriocins Kog1 and Kog2.

As a medium, RPMI 1640 medium supplemented with 10% FBS (Fetal Bovine Serum) (Biological industries, Haemek, Israel), 1% antibiotic and 1% L-glutamine was used. In each well of a 24-well plate, 400 µl of the medium was placed, and 100,000 cells/well of mouse-derived RAW264.7 macrophage-like cells were inoculated thereto.

The bacteriocin Kog1 or Kog2, which was the same as in Example 1, was incubated in an Eppendorf tube under each of the following 4 conditions together with *Porphyromonas gingivalis* LPS (manufactured by InvivoGen) (hereinafter referred to as P.g-LPS) and the same medium as described above, at 37° C. under a gas phase of 5% $CO_2$ for 2 hours: (1) 100 ng/ml P.g-LPS positive control; (2) 100 ng/ml P.g-LPS+5 µM Kog1 or Kog2; (3) 100 ng/ml P.g-LPS+10 µM Kog1 or Kog2; (4) 100 ng/ml P.g-LPS+20 µM Kog1 or Kog2.

The above-described medium placed in each well of the 24-well plate was removed using a pipetteman, and the medium in the Eppendorf tube for each of the 4 conditions described above was placed in the plate, followed by culturing the cells in the well plate at 37° C. under a gas phase of 5% $CO_2$ for 12 hours. Thereafter, the culture supernatant was collected, and the amount of a chemokine ccl2 or the amount of a cytokine TNF-α secreted into the medium was quantified by the ELISA method by measuring the absorbance at 450 nm using a microplate reader. Since both ccl2 and TNF-α are involved in formation of inflammation, analysis of the relationship between the endotoxin LPS and the bacteriocins Kog1 and Kog2 is possible.

Figure 9:
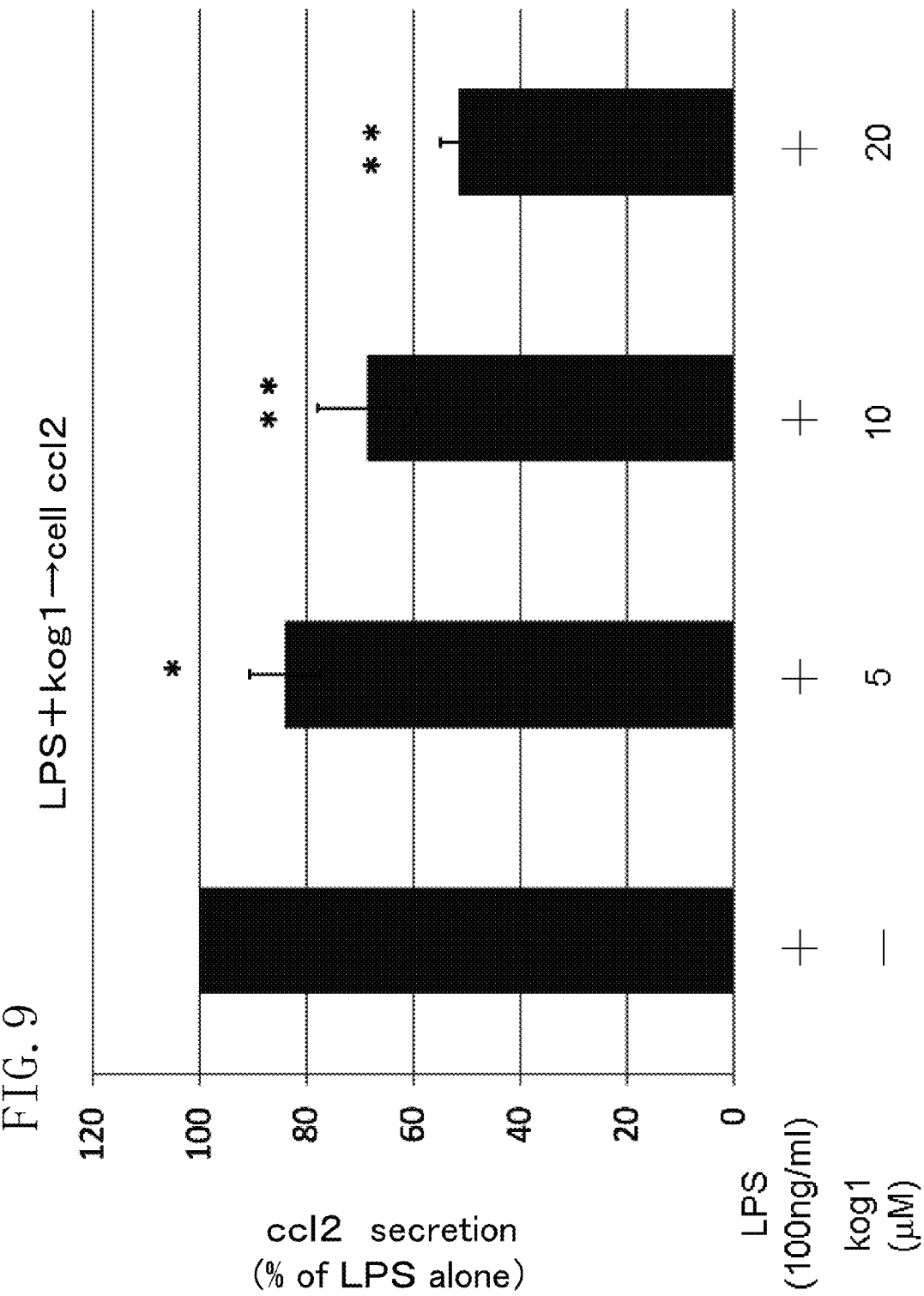
FIG. 9 is a diagram showing the relationship between the amounts of LPG and Kog1 (SEQ ID NO:1) and the amount of secretion of ccl2 observed in Example 7.

FIG. 9 is a diagram showing the relationship between the amounts of LPS and Kog1 and the amount of secretion of ccl2 observed in Example 7. That is, FIG. 9 shows the amount of the chemokine ccl2 secreted in the cases where incubation was carried out using LPS and Kog1 for 2 hours (the amount observed with 0 µM Kog1 is regarded as 100%) ("LPS+kog1→cell ccl2"). In FIG. 9, * (level of significance)= $p<0.05$, **(level of significance)=$p<0.01$, and n=3. As shown in FIG. 9, as the amount of Kog1 added increased, the amount of the chemokine ccl2 secreted decreased. That is, the bacteriocin Kog1 was revealed to have an action to inactivate LPS.

Figure 10:
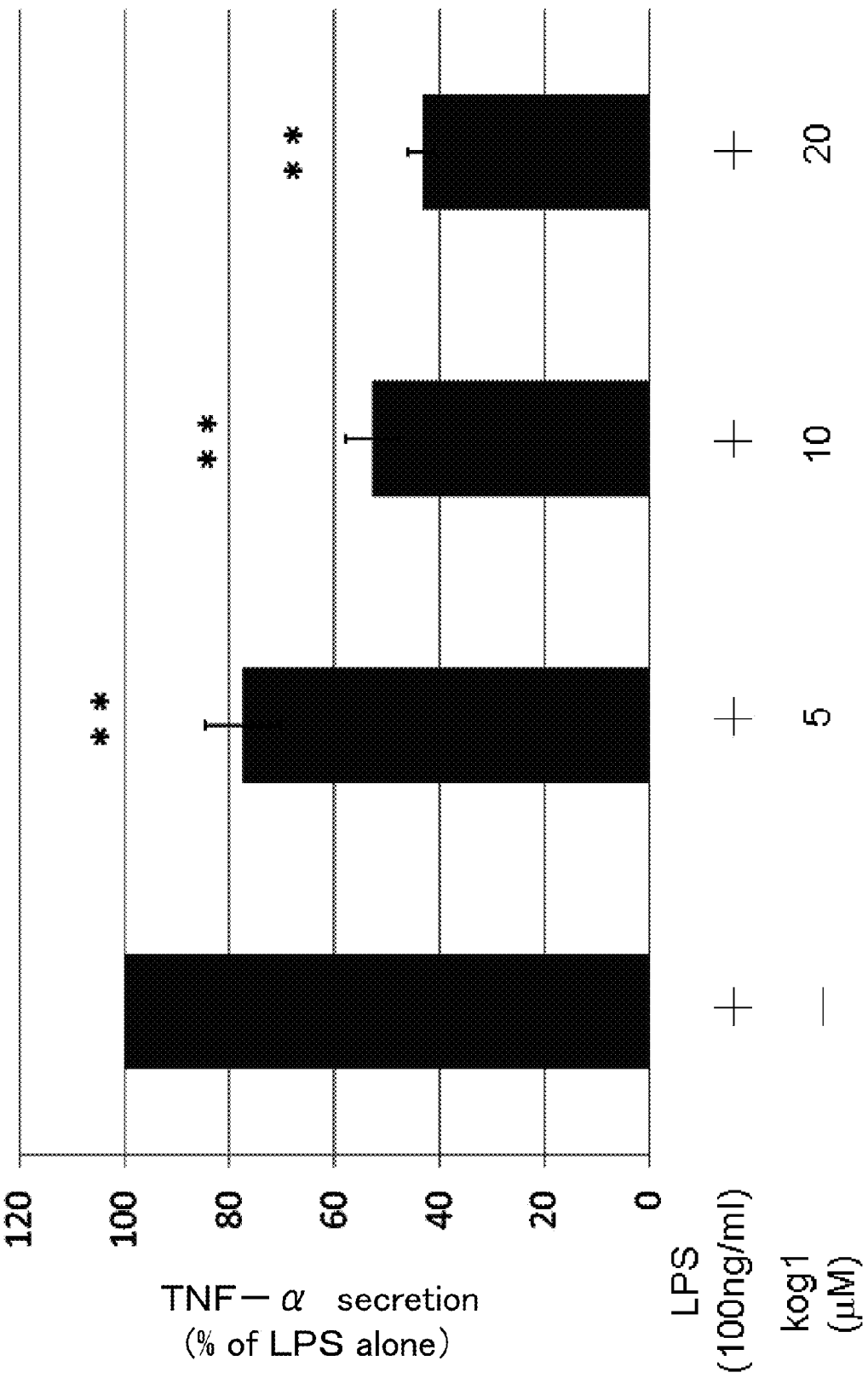
FIG. 10 is a diagram showing the relationship between the amounts of LPS and Kog1 (SEQ ID NO:1) and the amount of secretion of TNF-α observed in Example 7.

FIG. 10 is a diagram showing the relationship between the amounts of LPS and Kog1 and the amount of secretion of TNF-α observed in Example 7. That is, FIG. 10 shows the amount of the cytokine TNF-α secreted in the cases where incubation was carried out using LPS and Kog1 for 2 hours (the amount observed with 0 μM Kog1 is regarded as 100%) ("LPS+kog1→cell TNF-α"). In FIG. 10, ** (level of significance)=p<0.01, and n=3. As shown in FIG. 10, as the amount of Kog1 added increased, the amount of the cytokine TNF-α secreted decreased. That is, similarly to the results shown in FIG. 9, the bacteriocin Kog1 was revealed to have an action to inactivate LPS.

Figure 11:
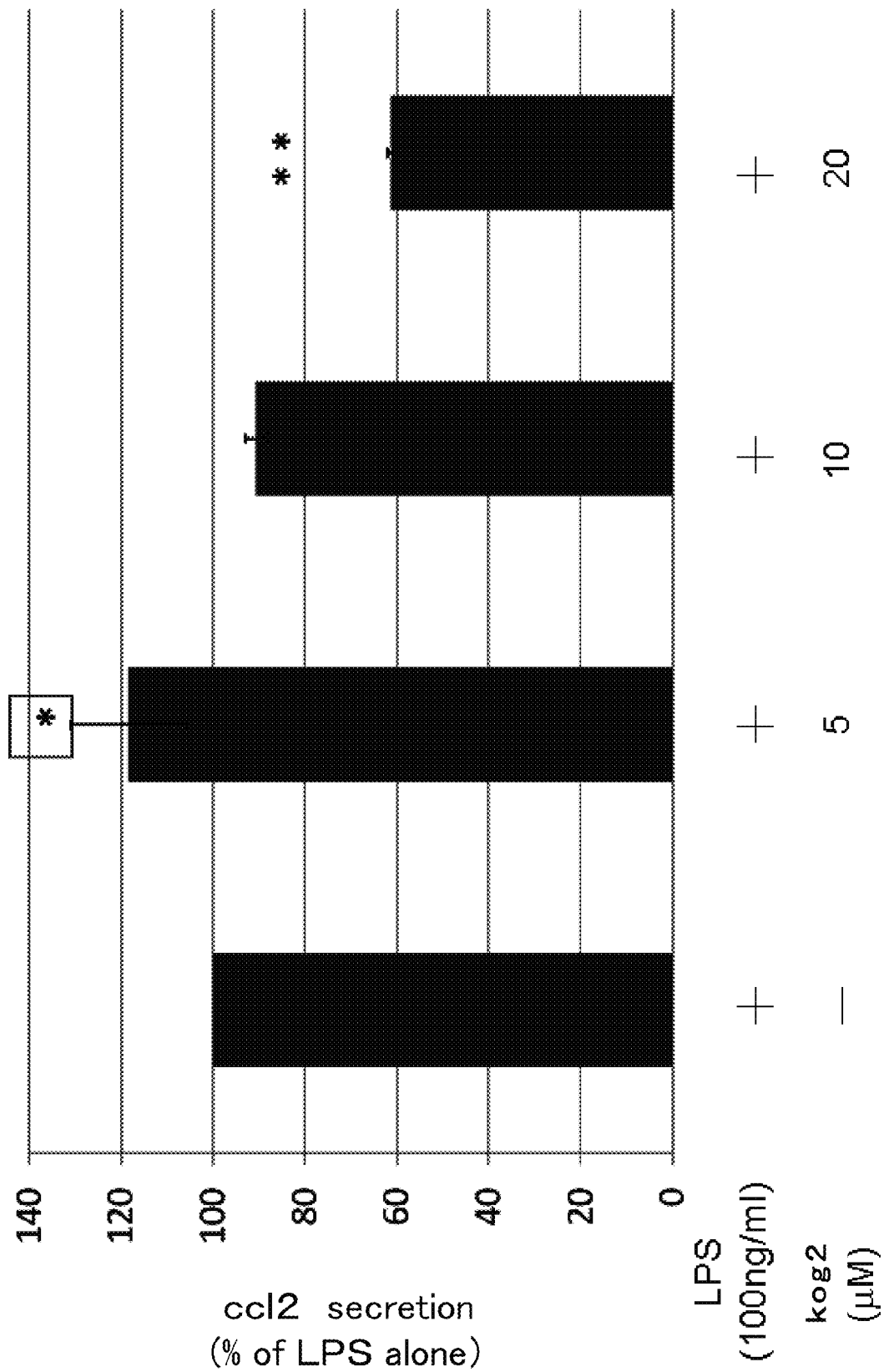
FIG. 11 is a diagram showing the relationship between the amounts of LPS and Kog2 (SEQ ID NO:2) and the amount of secretion of ccl2 observed in Example 8.

FIG. 11 is a diagram showing the relationship between the amounts of LPS and Kog2 and the amount of secretion of ccl2 observed in Example 7. That is, FIG. 11 shows the amount of the chemokine ccl2 secreted in the cases where incubation was carried out using LPS and Kog2 for 2 hours (the amount observed with 0 μM Kog2 is regarded as 100%) ("LPS+kog2→cell ccl2"). In FIG. 11, * (level of significance)=p<0.05, ** (level of significance)=p<0.01, and n=3. It is suggested, as shown in FIG. 11, that the amount of the chemokine ccl2 secreted increases when the amount of Kog2 added is small (5 μM), but, when the amount of Kog2 added exceeds a certain level, the amount of ccl2 decreases as the amount of Kog2 added increases. That is, it was revealed that Kog2, when added in a large amount, also has an action to inactivate LPS.

Figure 12:
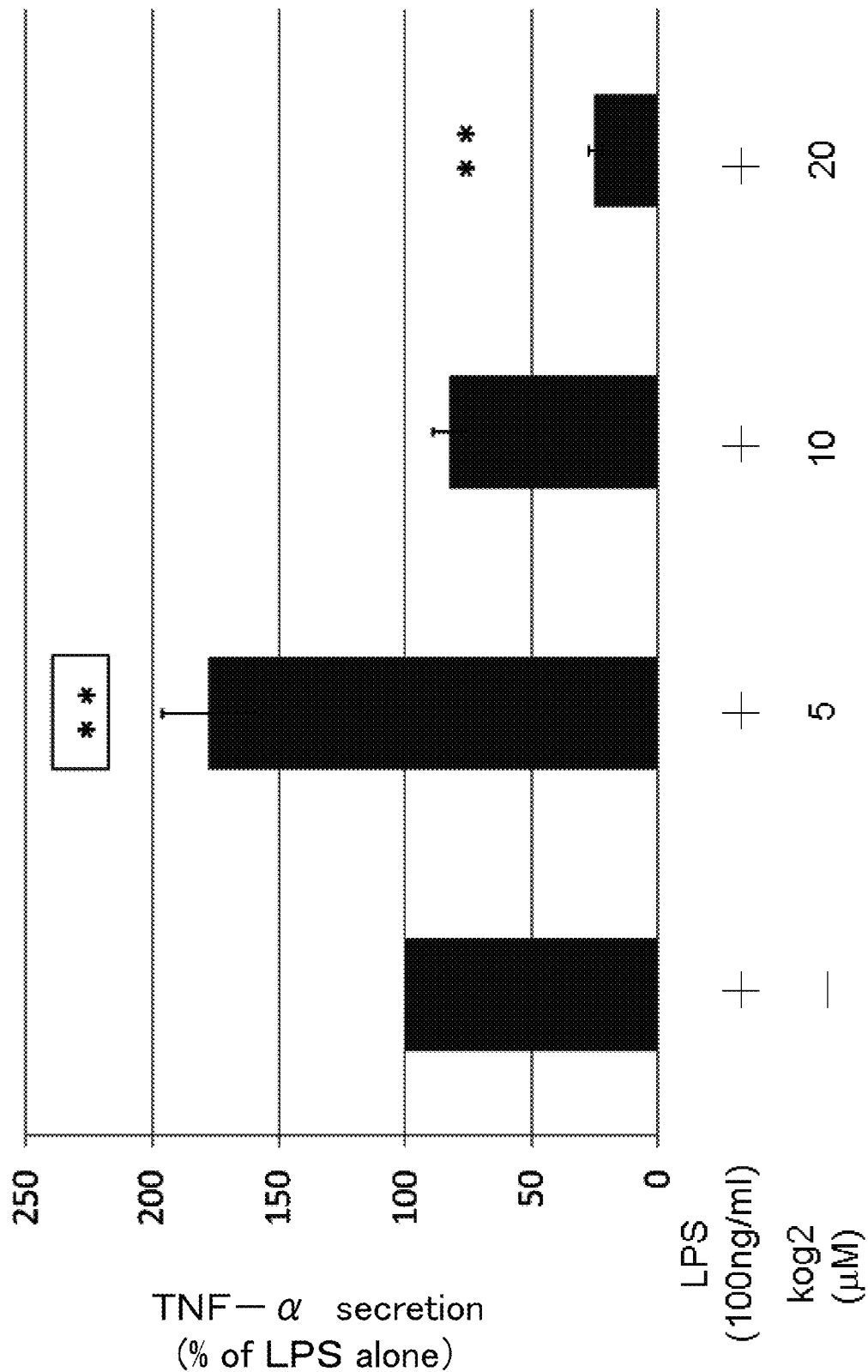
FIG. 12 is a diagram showing the relationship between the amounts of LPS and Kog2 (SEQ ID NO:2) and the amount of secretion of TNF-α observed in Example 8.

FIG. 12 is a diagram showing the relationship between the amounts of LPS and Kog2 and the amount of secretion of TNF-α observed in Example 7. That is, FIG. 12 shows the amount of the cytokine TNF-α secreted in the cases where incubation was carried out using LPS and Kog2 for 2 hours (the amount observed with 0 μM Kog2 is regarded as 100%) ("LPS+kog2→cell TNF-α"). In FIG. 12, ** (level of significance)=p<0.01, and n=3. It is suggested, as shown in FIG. 12, that the amount of the cytokine TNF-α secreted increases when the amount of Kog2 added is small (5 μM), but, when the amount of Kog2 added exceeds a certain level, the amount of TNF-α decreases as the amount of Kog2 added increases. That is, similarly to the results shown in FIG. 11, it was revealed that Kog2, when added in a large amount, has an action to inactivate LPS.

Figure 13:
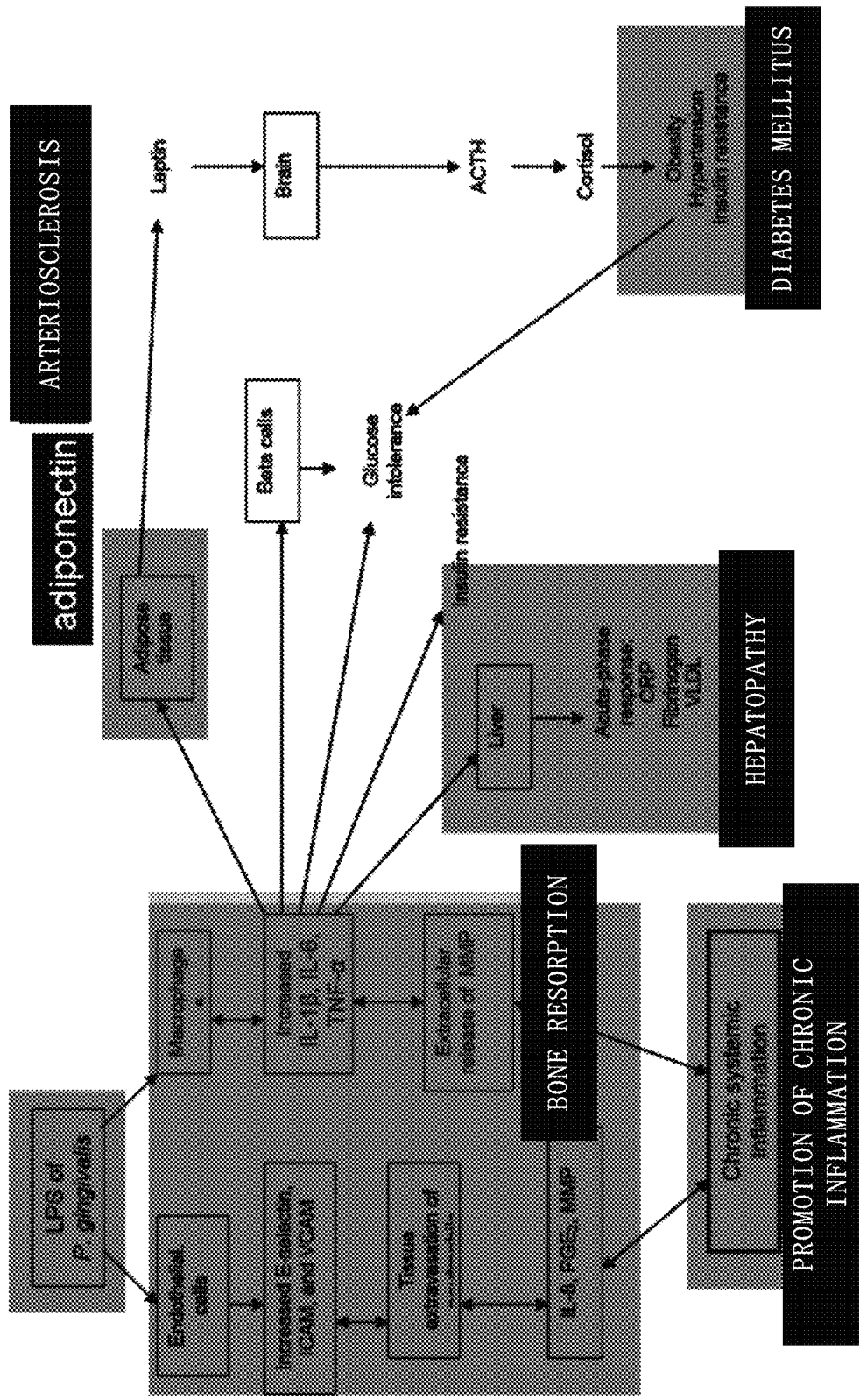
FIG. 13 is a diagram showing association of LPS with various diseases caused thereby.

Thus, from the results of FIG. 9 to FIG. 12, it became clear that the excellent antimicrobial activity and the like of the bacteriocins Kog1 and Kog2 are associated at least with the action of the bacteriocins Kog1 and Kog2 to inactivate LPS. Further, the fact that the bacteriocins Kog1 and Kog2 have the action to inactivate LPS suggests possible utilization of the bacteriocins Kog1 and Kog2 in prophylactic or therapeutic methods for other diseases in which involvement of the endotoxin LPS is known at present. Examples of such diseases include, in addition to oral diseases, bone resorption, promotion of chronic inflammation, hepatopathy, diabetes mellitus and arteriosclerosis. FIG. 13 is a diagram showing association of LPS with various diseases caused thereby. As shown in FIG. 13, the endotoxin LPS is involved in many diseases and therapeutic mechanisms via various substances.

Example 8

Thus, the present inventor investigated whether or not Kog2 influences, other than the oral diseases, differentiation into osteoblasts, by real-time quantitative RT (Reverse transcriptase)-PCR.

MC3T3-E1 cells, which are mouse-derived osteoblast-like cells, were used. The MC3T3-E1 cells were cultured in α-modified Eagle's Medium (α-MEM) supplemented with 10% FBS (Biological industries, Haemek, Israel), L-glutamine, antibiotic mixture (Invitrogen), 50 μg/ml ascorbic acid (Sigma), and 0 nM, 250 nM, 500 nM or 1000 nM Kog2, at 37° C. under 5% $CO_2$ on plastic or titanium. From the thus cultured MC3T3-E1 cells, total RNA was extracted using TRIzol reagent (Invitrogen), and cDNA was then prepared using ReverTra Ace reverse transcriptase (Toyobo Co., Ltd.). Subsequently, the prepared cDNA was used for analyzing expression of Type-I collagen, which is a differentiation marker for osteoblasts, and of β-actin, which is an endogenous control, by real-time quantitative RT-PCR.

In the real-time quantitative RT-PCR, Type-I collagen was analyzed using the forward primer shown in SEQ ID NO: 8, the reverse primer shown in SEQ ID NO: 9 and the probe shown in SEQ ID NO: 10. β-actin was analyzed using the forward primer shown in SEQ ID NO: 11, the reverse primer shown in SEQ ID NO: 12, and the probe shown in SEQ ID NO: 13.

Figure 14:
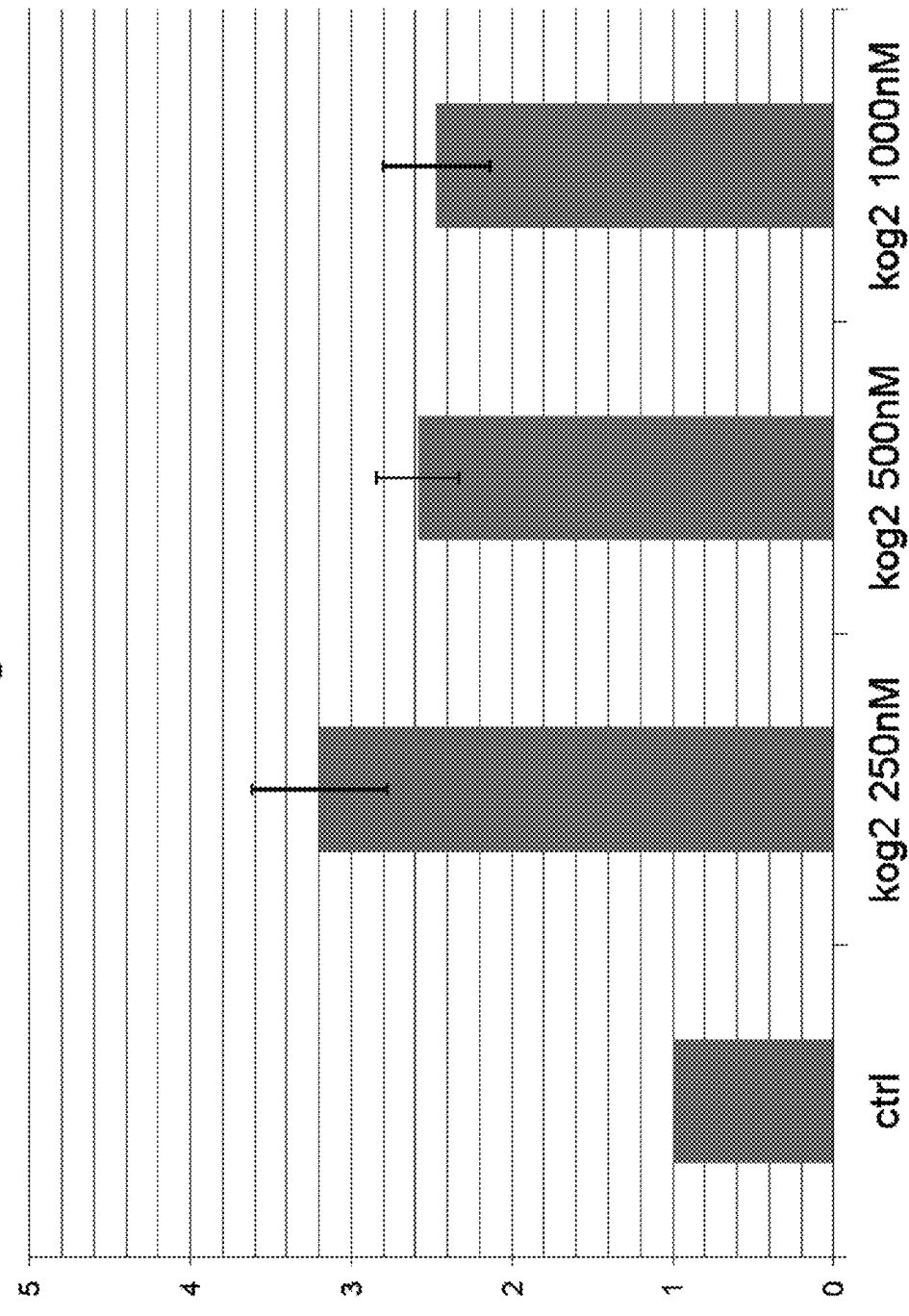
FIG. 14 is a diagram showing the value of Type I collagen/β-actin observed by real-time quantitative RT-PCR of cells treated with Kog2 (SEQ ID NO:2) in Example 8.

FIG. 14 is a diagram showing the value of Type I collagen/β-actin observed by the real-time quantitative RT-PCR in Example 8. As shown in FIG. 14, the value of Type I collagen/β-actin was 3 times higher in the case where Kog2 was added at 250 nM than in the case where Kog2 was not added (ctrl (0 μM)). It was found in the present experiment that addition of Kog2 at about 250 nM best promotes differentiation into osteoblasts. That is, it is sufficiently suggested that the bacteriocin Kog2 is also applicable to various bone diseases.

Example 9

Further, the present inventor carried out a boiling experiment to investigate whether or not the bacteriocins Kog1 and Kog2 similarly have antimicrobial activity after heating.

In Example 9, antimicrobial activity against the *Candida albicans* MYA274 strain was investigated. The *Candida albicans* MYA274 strain was precultured in Sabouraud dextrose broth (Difco) at 37° C. for 24 hours, and then washed twice with MQ water, followed by being prepared such that OD600 is 0.3 ($1.0 \times 10^7$ cells/ml).

In Example 9, the bacteriocin Kog1 or Kog2, or the *Lactobacillus rhamnosus* KO1 strain or KO3 strain, was not directly used. Instead, a lactic acid bacterium medium containing the *Lactobacillus rhamnosus* KO3 strain, 8020 yogurt (liquid type), was used in the experiment More specifically, the 8020 yogurt (liquid type) was prepared by adding the *Lactobacillus rhamnosus* KO3 strain at a concentration of 1% and YF-L811 starter at a concentration of 1% to the 15% skim milk+3% glucose medium, and then performing culture at 35° C. for 2 days. Even more specifically, the 8020 yogurt contained a high-fructose corn syrup, dairy product, sugar, stabilizer (pectin), acidulant and flavoring agent as other materials, and was prepared such that the 8020 yogurt had a brix of 17.4%, lactic acid acidity of 0.57%, pH of 3.96, and milk solids non-fat of 3.0%.

Such 8020 yogurt (liquid type) was centrifuged to obtain a supernatant from which the lactic acid bacterium was removed (hereinafter referred to as Supernatant B). In the experiment, Supernatant B and a sample prepared by boiling Supernatant B at 100° C. for 20 minutes (hereinafter referred to as Supernatant Boil) were used. It should be noted that, based on the results in the above Examples, Supernatant B is considered to contain the bacteriocins Kog1 and Kog2 extracted from the *Lactobacillus rhamnosus* KO3 strain.

In order to study changes in the antimicrobial activity by boiling, the following 3 kinds of samples were placed in a 24-well plate, and the value of ATP (pmol/L) after 24 hours of incubation at 37° C. was measured. The 3 kinds of samples were: 1) a mixture containing 1 ml of Sabouraud broth, 1 ml of Supernatant B and 50 µl of the prepared liquid of the *Candida albicans* MYA274 strain; 2) a mixture containing 1 ml of Sabouraud broth, 1 ml of Supernatant Boil and 50 µl of the prepared liquid of the *Candida albicans* MYA274 strain; and 3) a control mixture containing 1 ml of Sabouraud broth, 1 ml of the 15% skim milk+3% glucose medium and 50 µl of the prepared liquid of the *Candida albicans* MYA274 strain.

Figure 15:
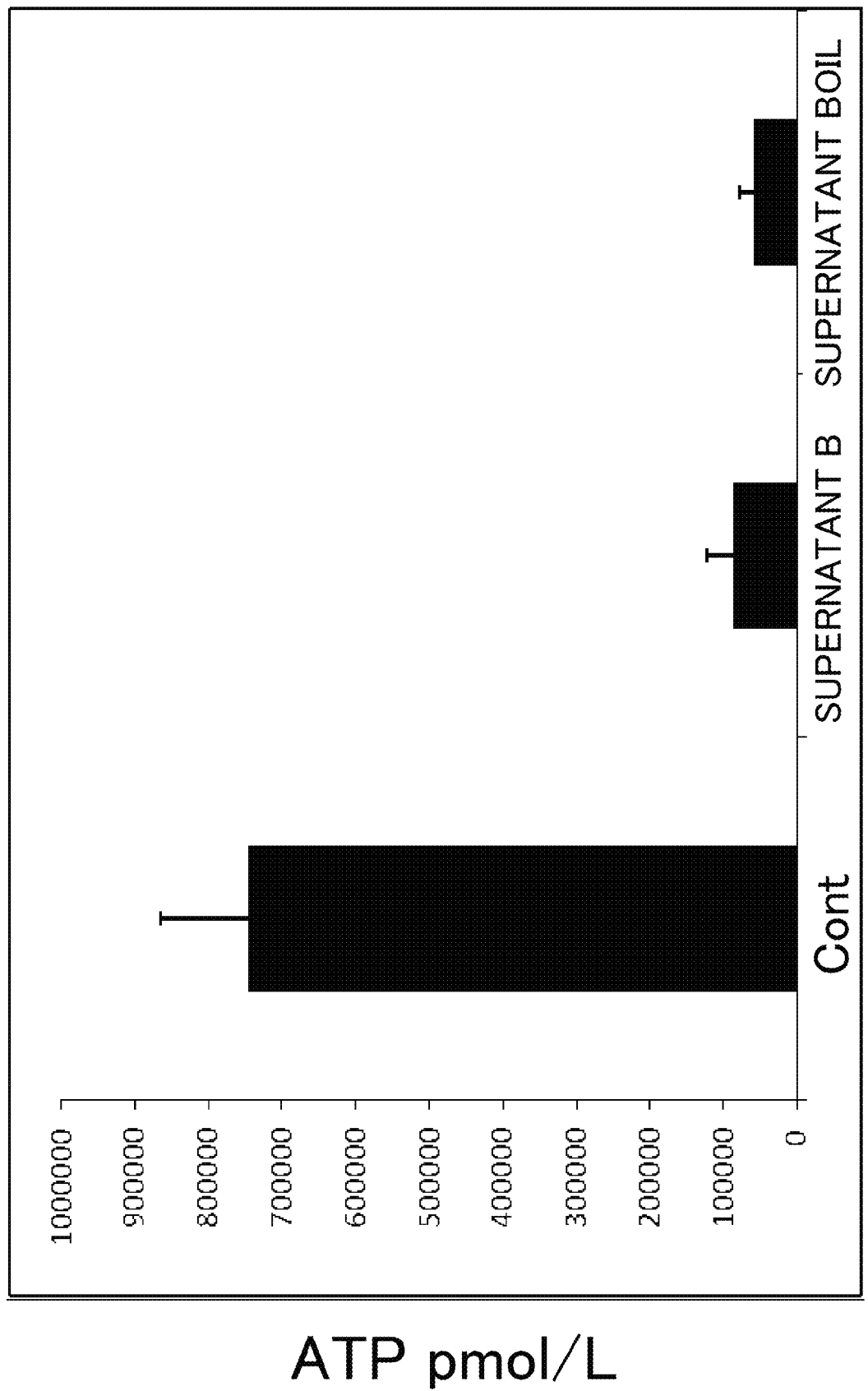
FIG. 15 is a diagram showing data on the result for heat resistance tested by a boiling experiment in Example 9.

FIG. 15 is a diagram showing heat resistance data obtained by the boiling experiment in Example 9. The heat resistance data are based on the mean±SD calculated for 4 replicates of each sample. As shown in FIG. 15, the ATP level measured for Supernatant Boil, prepared by 20 minutes of boiling at 100° C., was similar to the ATP level measured for Supernatant B, so that it was confirmed that even Supernatant Boil, prepared by boiling, has high antimicrobial activity similar to Supernatant B. That is, it was confirmed that the bacteriocins Kog1 and Kog2 still maintain antimicrobial activity after heating.

The present invention is not limited by the explanations in the embodiments and Examples described above. Various modified modes are also included in the present invention within the range where the modes do not depart from the description of claims and are easily inferred by the skilled person.

The contents of the papers, Laid-open Patent Publications and the like specified in the present description are hereby cited in their entirety.

The present application is based on Japanese Patent Application No. 2011-27882, filed on Feb. 10, 2011, and Japanese Patent Application No. 2011-184655, filed on Aug. 26, 2011. The description, claims and drawings in Japanese Patent Application No. 2011-27882 and Japanese Patent Application No. 2011-184655 are hereby incorporated by reference in their entirety.

INDUSTRIAL APPLICABILITY

The present inventors discovered that Kog1, which has the amino acid sequence shown in SEQ ID NO: 1, and Kog2, which has the amino acid sequence shown in SEQ ID NO: 2, are functioning as bacteriocins in the *Lactobacillus rhamnosus* KO3 strain (an application for deposition of the strain was submitted to Patent Microorganisms Depositary, National Institute of Technology and Evaluation as of Jun. 10, 2009, and accepted under accession No. NITE BP-771), which bacteriocins have wide antimicrobial spectra and high antimicrobial activity at low concentration, and are less likely to produce resistant microorganisms. Further, the present inventors succeeded in separation and identification of a novel lactic acid bacterial strain that similarly produces Kog1 and Kog2, the *Lactobacillus rhamnosus* KO1 strain (an application for deposition of the strain was submitted to Patent Microorganisms Depositary, National Institute of Technology and Evaluation as of Jan. 24, 2011, and accepted under accession No. NITE P-1065).

Thus, the present invention enables to provide a bacteriocin that is capable of being easily mass-produced, which bacteriocin has a wide antimicrobial spectrum and is less likely to produce resistant microorganisms; a composition for prophylaxis, amelioration and/or therapy of oral diseases comprising the bacteriocin (including pharmaceutically acceptable derivatives and the like thereof) as an effective component, a gene encoding the bacteriocin, a recombinant expression vector obtained by incorporation of the gene, a host cell comprising the recombinant expression vector, a transformant produced by transformation with the recombinant expression vector, and a method for producing the bacteriocin. Further, the present invention enables to provide a novel lactic acid bacterial strain that produces the bacteriocin, the *Lactobacillus rhamnosus* KO1 strain. Further, since the bacteriocin of the present invention has high heat resistance, industrial processing of the bacteriocin is easy. In particular, because of such heat resistance, processing of the bacteriocin of the present invention into gummy jellies, troches, tablets, candies and chewing gums, which requires heating, is possible without decreasing the antimicrobial effect. Further, since addition of the bacteriocin to, for example, foods to be cooked such as rice and soup does not decrease the effect of the bacteriocin, application of the bacteriocin to various uses is expected.

---

The invention claimed is:

1. A method for amelioration and/or therapy of diseases of the oral cavity caused by cariogenic bacteria, periodontal disease bacteria, and/or *Candida*, the method comprising:
administering an isolated basic antimicrobial peptide comprising the amino acid sequence of SEQ ID NO:1 or SEQ ID NO:2, or a pharmaceutically acceptable salt of the basic antimicrobial peptide, to a subject with a disease of the oral cavity, wherein the basic antimicrobial peptide is antimicrobial to cariogenic bacteria, periodontal disease bacteria, and/or *Candida*.

2. The method according to claim 1 wherein the basic antimicrobial peptide has an isoelectric point of not less than 12.

3. The method according to claim 1, wherein the cariogenic bacteria is *Streptococcus mutans* or *Streptococcus sobrinus*.

4. The method according to claim 1, wherein the periodontal disease bacteria is *Aggregatibacter actinomycetemcomitans* Hudoe001, *Porphyromonas gingivalis*, *Prevotella intermedia*, *Treponema denticola*, *Tannerella forsythensis*, *Actinobacillus actinomycetemcomitans*, or *Fusobacterium nucleatum*.

5. The method according to claim 1, wherein the *Candida* is *Candida albicans*, *Candida glabrata*, or *Candida tropicalis*.

6. The method according to claim 1, wherein the basic antimicrobial peptide is formulated for oral administration and comprises at least one additional component suitable for incorporation in a food, pharmaceutical, or oral composition.

7. The method according to claim 1, wherein the disease of the oral cavity is dental caries, gingivitis, periodontitis, glossitis, thrush, or angular cheilitis.

8. A method for producing a basic antimicrobial peptide of SEQ ID NO: 1 or SEQ ID NO: 2, the method comprising: (a) culturing *Lactobacillus rhamnosus* and (b) extracting the basic antimicrobial peptide of SEQ ID NO: 1 or SEQ ID NO: 2 from the *Lactobacillus rhamnosus* of step (a).

9. The method for producing the basic antimicrobial peptide of SEQ ID NO: 1 or SEQ ID NO: 2 according to claim 8, wherein the *Lactobacillus rhamnosus* is a *Lactobacillus rhamnosus* KO1 strain (accession No. NITE P-1065) and/or a *Lactobacillus rhamnosus* KO3 strain (accession No. NITE BP-771).

10. The method for producing the basic antimicrobial peptide of SEQ ID NO: 1 or SEQ ID NO: 2 according to claim 8, wherein step (a) further comprises adding killed *Candida* cells.

11. The method for producing the basic antimicrobial peptide of SEQ ID NO: 1 or SEQ ID NO: 2 according to claim 9, wherein step (a) further comprises adding killed *Candida* cells.

* * * * *

SEQUENCE LISTING

<160> NUMBER OF SEQ ID NOS: 13

<210> SEQ ID NO 1
<211> LENGTH: 48
<212> TYPE: PRT
<213> ORGANISM: Lactobacillus rhamnosus

<400> SEQUENCE: 1

Met Ala Lys Ala Arg Pro Ser Arg Pro Arg Pro Leu Thr Leu Arg Ser
1               5                   10                  15

Leu Thr Ala Pro Ala His Ala His Lys Lys Trp Ala Ser Arg Trp Ile
            20                  25                  30

Leu Ser Met Arg Leu Ala Arg Val Phe Gly Ile Glu Lys Pro His Gly
        35                  40                  45

<210> SEQ ID NO 2
<211> LENGTH: 41
<212> TYPE: PRT
<213> ORGANISM: Lactobacillus rhamnosus

<400> SEQUENCE: 2

```
Met Thr Lys Val Arg Ser Ser Arg Leu Arg Pro Leu Thr Leu Arg Leu
1               5                   10                  15

Leu Ser Ala Pro Ala Arg Ala Gln Phe Leu Thr Ile Ala Cys Arg Ala
            20                  25                  30

Ile Leu Arg Tyr Asp Leu Ile Asn Ser
        35                  40

<210> SEQ ID NO 3
<211> LENGTH: 147
<212> TYPE: DNA
<213> ORGANISM: Lactobacillus rhamnosus

<400> SEQUENCE: 3
atggccaaag cccggccatc acgtccaagg ccgcttacac tccgatcctt aaccgcgcca      60
gctcacgctc acaaaaaatg ggccagccgt tggattttat ccatgcgact ggcccgagtt     120
ttcggtatcg aaaagccgca tggatga                                         147

<210> SEQ ID NO 4
<211> LENGTH: 126
<212> TYPE: DNA
<213> ORGANISM: Lactobacillus rhamnosus

<400> SEQUENCE: 4
atgaccaaag tacggtcatc acgcctgagg ccacttacac tccgacttct aagcgcgccg      60
gctcgcgctc agttcctgac gatcgcgtgc cgagccattc tgcgttatga tttaattaat     120
agttaa                                                                126

<210> SEQ ID NO 5
<211> LENGTH: 25
<212> TYPE: PRT
<213> ORGANISM: Artificial sequence
<220> FEATURE:
<223> OTHER INFORMATION: Antimicrobial peptide

<400> SEQUENCE: 5

Phe Lys Cys Arg Arg Trp Gln Trp Arg Met Lys Lys Leu Gly Ala Pro
1               5                   10                  15

Ser Ile Thr Cys Val Arg Arg Ala Phe
            20                  25

<210> SEQ ID NO 6
<211> LENGTH: 24
<212> TYPE: PRT
<213> ORGANISM: Artificial sequence
<220> FEATURE:
<223> OTHER INFORMATION: Antimicrobial peptide

<400> SEQUENCE: 6

Asp Ser His Glu Lys Arg His His Gly Tyr Lys Arg Lys Phe His Glu
1               5                   10                  15

Lys His His Ser His Arg Gly Tyr
            20

<210> SEQ ID NO 7
<211> LENGTH: 14
<212> TYPE: PRT
<213> ORGANISM: Artificial sequence
<220> FEATURE:
<223> OTHER INFORMATION: Antimicrobial peptide

<400> SEQUENCE: 7
```

Lys Arg Leu Phe Arg Arg Trp Gln Trp Arg Met Lys Lys Tyr
1               5                   10

<210> SEQ ID NO 8
<211> LENGTH: 21
<212> TYPE: DNA
<213> ORGANISM: Artificial sequence
<220> FEATURE:
<223> OTHER INFORMATION: Forward primer for type 1 collagen

<400> SEQUENCE: 8
aacccgaggt atgcttgatc t                                    21

<210> SEQ ID NO 9
<211> LENGTH: 20
<212> TYPE: DNA
<213> ORGANISM: Artificial sequence
<220> FEATURE:
<223> OTHER INFORMATION: Reverse primer for type 1 collagen

<400> SEQUENCE: 9
ccagttcttc attgcattgc                                      20

<210> SEQ ID NO 10
<211> LENGTH: 20
<212> TYPE: DNA
<213> ORGANISM: Artificial sequence
<220> FEATURE:
<223> OTHER INFORMATION: Probe for type 1 collagen

<400> SEQUENCE: 10
cacggctgtg tgcgatgacg                                      20

<210> SEQ ID NO 11
<211> LENGTH: 20
<212> TYPE: DNA
<213> ORGANISM: Artificial sequence
<220> FEATURE:
<223> OTHER INFORMATION: Forward primer for beta-actin

<400> SEQUENCE: 11
ccacactgtg cccatctacg                                      20

<210> SEQ ID NO 12
<211> LENGTH: 20
<212> TYPE: DNA
<213> ORGANISM: Artificial sequence
<220> FEATURE:
<223> OTHER INFORMATION: Reverse primer for beta-actin

<400> SEQUENCE: 12
gtggtggtgg agctgtagcc                                      20

<210> SEQ ID NO 13
<211> LENGTH: 22
<212> TYPE: DNA
<213> ORGANISM: Artificial sequence
<220> FEATURE:
<223> OTHER INFORMATION: Probe for beta-actin

<400> SEQUENCE: 13
cctgcgtctg gacctggctg gc                                   22